US012611224B2

(12) United States Patent (10) Patent No.: US 12,611,224 B2

Su et al. (45) Date of Patent: Apr. 28, 2026

(54) VASCULAR OCCLUSION DETECTION FROM MOTORIZED SEPARATOR TORQUE MEASUREMENT SIGNAL

(71) Applicant: PENUMBRA, INC., Alameda, CA (US)

(72) Inventors: Bo-Yu Su, Alameda, CA (US); Vinita Verma, Pleasanton, CA (US)

(73) Assignee: PENUMBRA, INC., Alameda, CA (US)

( * ) Notice: Subject to any disclaimer, the term of this patent is extended or adjusted under 35 U.S.C. 154(b) by 143 days.

(21) Appl. No.: 18/441,164

(22) Filed: Feb. 14, 2024

(65) Prior Publication Data

US 2025/0255640 A1 Aug. 14, 2025

(51) Int. Cl.
*A61B 17/3207* (2006.01)
*A61B 17/00* (2006.01)
*A61B 17/22* (2006.01)
*A61B 90/00* (2016.01)

(52) U.S. Cl.
CPC ................. *A61B 17/320758* (2013.01); *A61B 2017/00017* (2013.01); *A61B 2017/22079* (2013.01); *A61B 2090/066* (2016.02)

(58) Field of Classification Search
CPC ...... A61B 17/320758; A61B 17/32075; A61B 17/320725; A61B 17/320783; A61B 2017/00017; A61B 2017/22079; A61B 2017/320775
See application file for complete search history.

(56) References Cited

U.S. PATENT DOCUMENTS

| | | | |
|---|---|---|---|
| 2019/0262032 A1* | 8/2019 | Carlson | G05B 13/021 |
| 2020/0289148 A1 | 9/2020 | Masubuchi et al. | |
| 2021/0007760 A1 | 1/2021 | Reisin | |
| 2022/0304719 A1* | 9/2022 | Hansen | A61B 17/320758 |
| 2023/0063577 A1 | 3/2023 | Pons | |
| 2023/0200843 A1* | 6/2023 | Tada | A61B 17/320758 |
| | | | 600/159 |
| 2023/0290496 A1 | 9/2023 | Tada et al. | |
| 2025/0169850 A1* | 5/2025 | Zheng | A61B 17/320758 |

FOREIGN PATENT DOCUMENTS

WO 2022/201011 A1 9/2022

* cited by examiner

*Primary Examiner* — Tuan V Nguyen

(74) *Attorney, Agent, or Firm* — HG LAW LLP

(57) ABSTRACT

Systems and methods are presented herein for detecting different engagement conditions of a separator instrument of a system. Processing circuitry is used to establish a baseline of one or more operational parameters for the separator instrument. At least one deviation from the established one or more baseline operational parameters of the separator instrument is identified using the processing circuitry. The processing circuitry is used to determine that the identified at least one deviation corresponds to at least one engagement condition of the separator instrument. An action is caused to be performed based on the determining by the processing circuitry.

18 Claims, 11 Drawing Sheets

205

205a

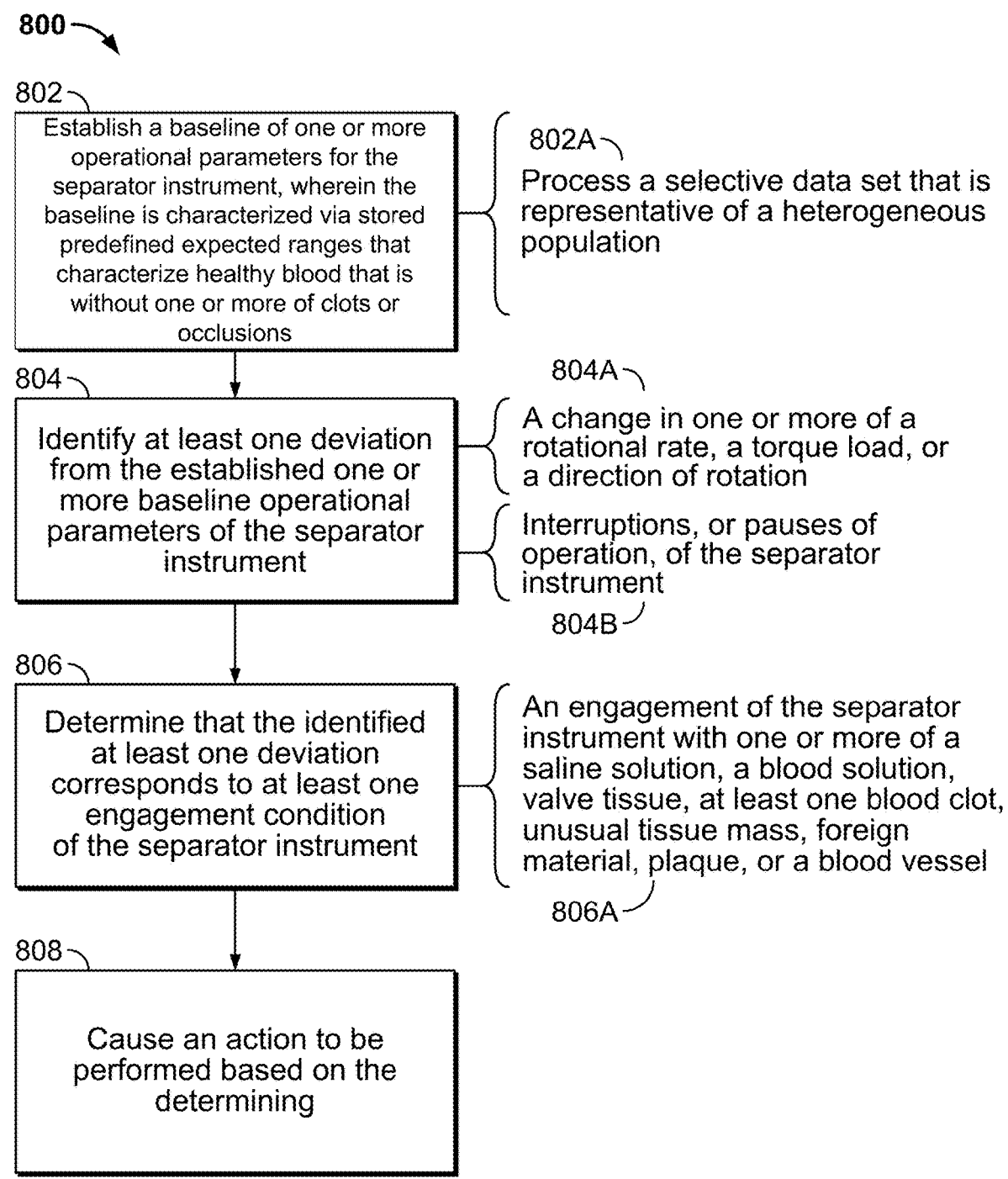

800

802
Establish a baseline of one or more operational parameters for the separator instrument, wherein the baseline is characterized via stored predefined expected ranges that characterize healthy blood that is without one or more of clots or occlusions 802A
Process a selective data set that is representative of a heterogeneous population 804
Identify at least one deviation from the established one or more baseline operational parameters of the separator instrument 804A
A change in one or more of a rotational rate, a torque load, or a direction of rotation Interruptions, or pauses of operation, of the separator instrument
804B 806
Determine that the identified at least one deviation corresponds to at least one engagement condition of the separator instrument An engagement of the separator instrument with one or more of a saline solution, a blood solution, valve tissue, at least one blood clot, unusual tissue mass, foreign material, plaque, or a blood vessel
806A 808
Cause an action to be performed based on the determining

FIG. 8

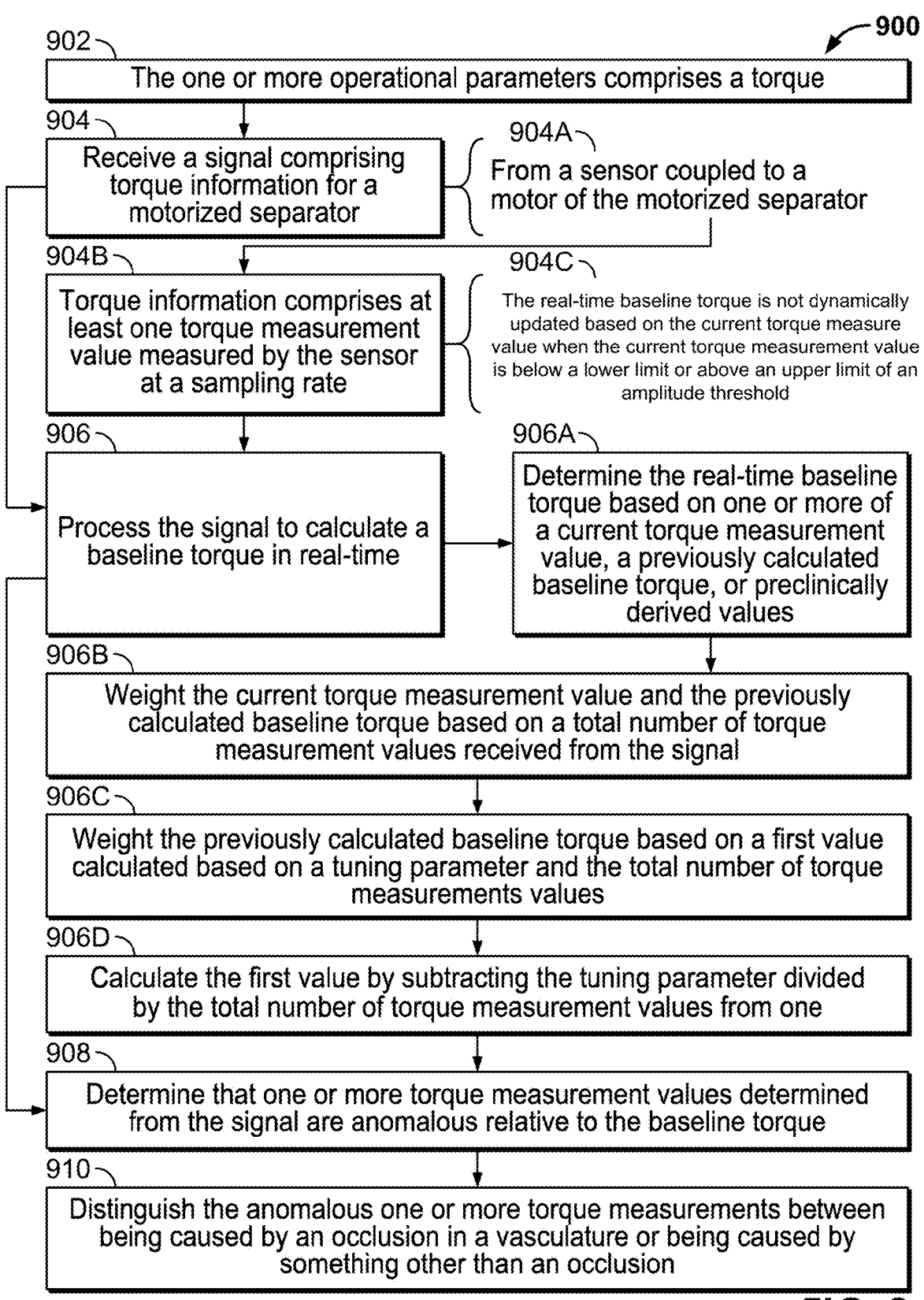

902 — The one or more operational parameters comprises a torque

900

904 — Receive a signal comprising torque information for a motorized separator

904A — From a sensor coupled to a motor of the motorized separator

904B — Torque information comprises at least one torque measurement value measured by the sensor at a sampling rate 904C — The real-time baseline torque is not dynamically updated based on the current torque measure value when the current torque measurement value is below a lower limit or above an upper limit of an amplitude threshold 906 — Process the signal to calculate a baseline torque in real-time 906A — Determine the real-time baseline torque based on one or more of a current torque measurement value, a previously calculated baseline torque, or preclinically derived values 906B — Weight the current torque measurement value and the previously calculated baseline torque based on a total number of torque measurement values received from the signal 906C — Weight the previously calculated baseline torque based on a first value calculated based on a tuning parameter and the total number of torque measurements values 906D — Calculate the first value by subtracting the tuning parameter divided by the total number of torque measurement values from one 908 — Determine that one or more torque measurement values determined from the signal are anomalous relative to the baseline torque 910 — Distinguish the anomalous one or more torque measurements between being caused by an occlusion in a vasculature or being caused by something other than an occlusion

Figures 10, 11:
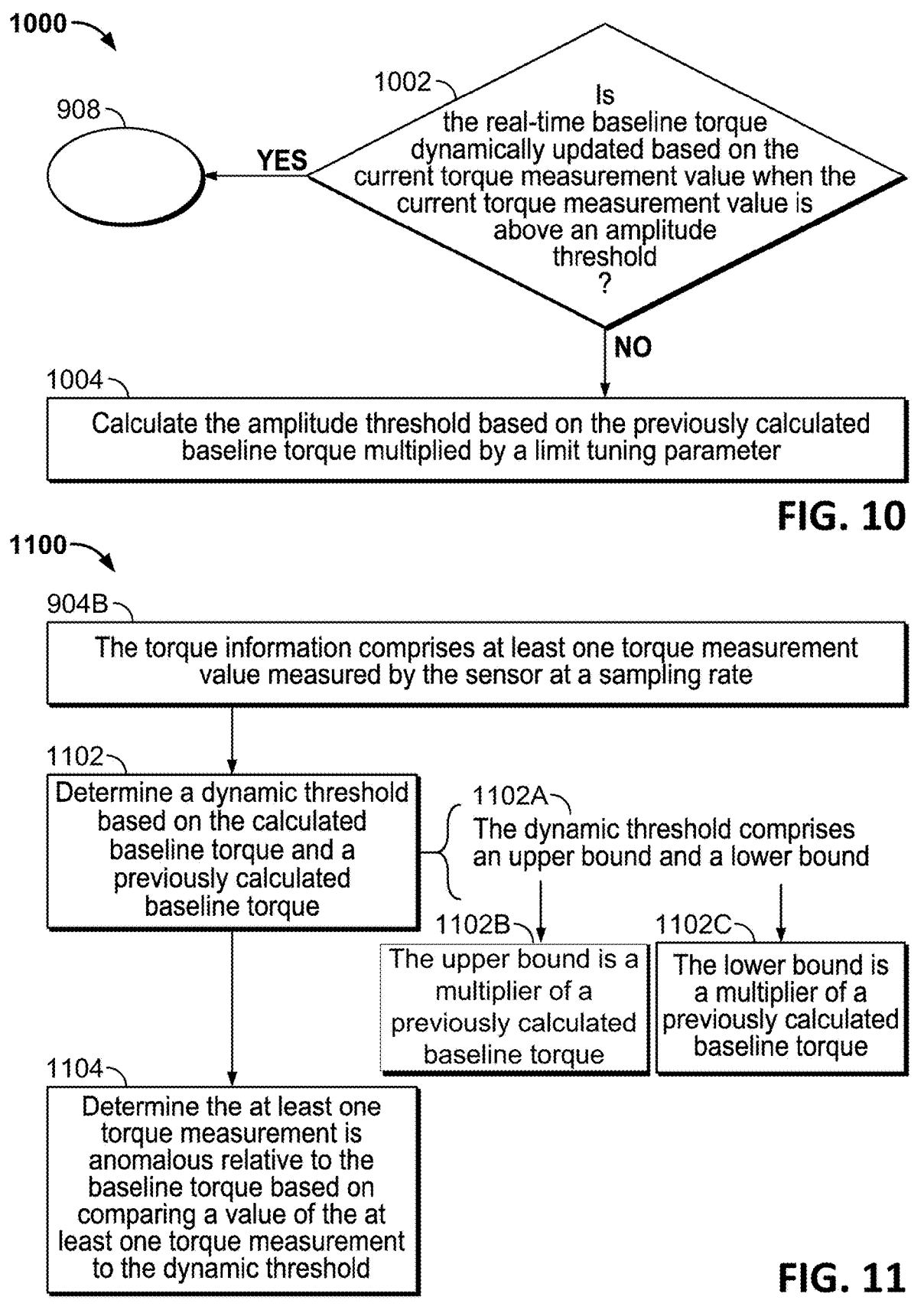

YES

1002 —↘
Is the real-time baseline torque dynamically updated based on the current torque measurement value when the current torque measurement value is above an amplitude threshold ?

NO

1004 —↘
Calculate the amplitude threshold based on the previously calculated baseline torque multiplied by a limit tuning parameter

904B —↘
The torque information comprises at least one torque measurement value measured by the sensor at a sampling rate 1102 —↘
Determine a dynamic threshold based on the calculated baseline torque and a previously calculated baseline torque 1102A —↘
The dynamic threshold comprises an upper bound and a lower bound 1102B —↘
The upper bound is a multiplier of a previously calculated baseline torque 1102C —↘
The lower bound is a multiplier of a previously calculated baseline torque 1104 —↘
Determine the at least one torque measurement is anomalous relative to the baseline torque based on comparing a value of the at least one torque measurement to the dynamic threshold

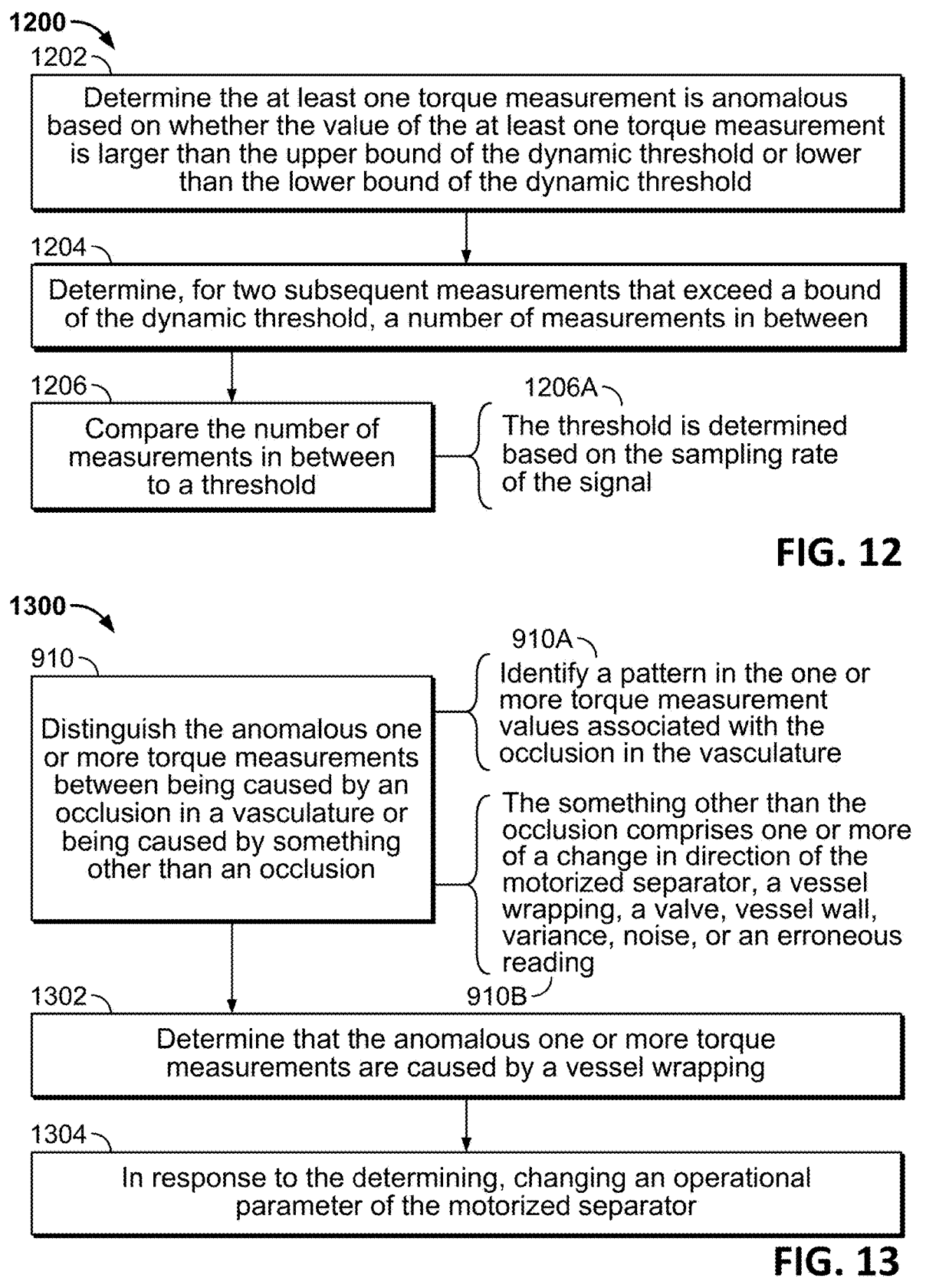

1202
Determine the at least one torque measurement is anomalous based on whether the value of the at least one torque measurement is larger than the upper bound of the dynamic threshold or lower than the lower bound of the dynamic threshold 1204
Determine, for two subsequent measurements that exceed a bound of the dynamic threshold, a number of measurements in between 1206
Compare the number of measurements in between to a threshold 1206A
The threshold is determined based on the sampling rate of the signal

910
Distinguish the anomalous one or more torque measurements between being caused by an occlusion in a vasculature or being caused by something other than an occlusion 910A
Identify a pattern in the one or more torque measurement values associated with the occlusion in the vasculature 910B
The something other than the occlusion comprises one or more of a change in direction of the motorized separator, a vessel wrapping, a valve, vessel wall, variance, noise, or an erroneous reading 1302
Determine that the anomalous one or more torque measurements are caused by a vessel wrapping 1304
In response to the determining, changing an operational parameter of the motorized separator

FIG. 13

VASCULAR OCCLUSION DETECTION FROM MOTORIZED SEPARATOR TORQUE MEASUREMENT SIGNAL

INTRODUCTION

The present disclosure is directed to systems and methods for cutting, collecting, and removing occlusive material from blood vessels and other body lumens, and more particularly, to systems and methods that modify operation of a device that removes occlusive material based on a detection of an engagement condition between, for example, a separator instrument and the occlusive material.

SUMMARY

Many factors can cause an undesirable buildup of occlusive material in the vascular system. For example, thrombosis (the formation of a blood clot) and atherosclerosis (buildup of fats, cholesterol and other substances on a wall of a blood vessel) are common conditions that can result in a buildup of material that at least partially blocks a blood vessel. These deposits restrict blood flow and pose a risk of fragmenting into the blood stream. If this fragmented material travels to the heart, brain, or lungs, the event can be fatal. An example of one such disease state is Deep Venous Thrombosis (DVT), where blood clots form in the deep (non-superficial) veins of the body, typically within the legs. DVT is commonly characterized by the build-up of large volumes of tough, chronic clot which impedes venous flow. As such, there exists a need for an effective treatment that not only addresses the complication but also prevents the proliferation and reoccurrence of further, related complications.

The removal of occlusive material from blood vessels and other body lumens has commonly been approached through treatments based on drug administration, filter implants, and catheter-based removal. Anticoagulant drugs, such as Heparin, are the most commonly prescribed treatments, e.g., for DVT. The administration of anticoagulants helps prevent a clot from growing and relies on the body's lysing processes to eliminate the clot. This process is expensive, slow acting, not effective against large or complete occlusions, and risks residual clot entering the blood stream to cause venous damage elsewhere.

Thrombus filter implantation is used as a preventative measure for those at risk of developing clots. These filters are surgically implanted, typically into the inferior vena cava. Filters function to capture clot and then allow the body's lysing processes to eliminate the clot. Although the use of these filters can greatly reduce the likelihood of clot fragments traveling to the heart or lungs, they often require the use of anticoagulant drugs in concert and therefore entail all the complications described above. Furthermore, poor rates of physician follow-up and patient compliance result in a low percentage of filters ever being retrieved.

Catheter-based interventions present an alternative treatment method. Catheters or catheter-based devices are percutaneously introduced into blood vessels and are maneuvered into direct contact with a target substance. For newly formed thrombus or unadhered and small plaque, the substance may be removed through a catheter via aspiration, mechanical capture, or other means. This approach has the benefit of quickly removing the target substances and the benefit of leaving behind little residual material, which could otherwise lead to reoccurrence or proliferation of related diseases. However, the limitations on the type and volume of occlusive material which can be successfully removed make it a non-viable approach to many disease states, such as a subset of DVT which can involve large, tough thrombus burdens.

Some catheter-based devices include rotating blades, high pressure water jets, laser ablation, or other aggressive means of breaking up the target material. Such methods are common in atherectomy-specific tools where the occlusion is formed by wall-adhered plaque. Many such devices can suffer from at least one of two shortcomings. Firstly, the methods of removing targeted substances once the substances are fragmented can be either ineffective or non-existent. For example, some devices have small lumens that are prone to clogging or inefficient pressure gradients that fail to pull dislodged clot or plaque into the system. If not removed, dislodged clot or plaque is released into downstream blood vessels and poses a risk for further complications. Secondly, devices that use blades to fragment a tough clot or plaque might lead to damage of the wall of a blood vessel.

For the reasons discussed above, there has existed an unmet need for methods and apparatus that remove a wide range of occlusive materials, including at least clot, thrombus, and atheroma, quickly and safely without damaging the surrounding blood vessels. Accordingly, a considerable improvement to the approaches described includes detecting different engagement conditions of a device that is designed to remove occlusive material and modifying operation of the device so as to avoid damaging healthy tissue that surrounds or is intertwined with the occlusive material.

Described herein, in accordance with various embodiments of this disclosure, is a method for detecting different engagement conditions of a device that is configured to remove occlusive material in a blood vessel (e.g., a separator instrument) and causing an action to be performed based on the determining (e.g., modifying operational parameters of the separator instrument to avoid damaging healthy tissue surrounding or intertwined with the occlusive material). Processing circuitry is used to establish a baseline of one or more operational parameters for the device, which can be a separator instrument. At least one deviation from the established one or more baseline operation parameters is identified using the processing circuitry. A determination is made using the processing circuitry that the identified at least one deviation corresponds to at least one engagement condition of the separator instrument. The processing circuitry causes an action to be performed based on the determining.

The device, in some embodiments, includes a catheter (e.g., a thrombectomy catheter), for use in a subject's vasculature includes a rotatable and/or axially movable cutting instrument. The cutting instrument may be a spiral-shaped (e.g., helical-shaped) cutting instrument such as a separator instrument. A rounded, spherical, substantially spherical, or partially spherical element at a distal end of the instrument can be connected to a body having a twisted shape (e.g., a spiral and/or helical shape). The cutting instrument is disposed in a lumen of the catheter and is configured for axial and/or rotational motion within the lumen between a proximal-most position and a distal-most position. In some embodiments, the cutting instrument can extend out slightly beyond the distal-most position of the lumen such that at least part of the cutting instrument extends external to the lumen of the catheter. Additionally, or alternatively, the cutting instrument can be flush or recessed into the catheter. Accordingly, the separator instrument may incorporate a positive displacement pump, or other related architecture, for displacing fluids with viscosities greater than water or other room temperature liquids. In some examples, the body includes at least one edge configured to promote the movement of a target substance towards a proximal end of the lumen upon contact, or close proximity to, the target substrate. When processing circuitry is coupled to the cutting instruction and power (e.g., electrical power) is provided, the cutting instrument deploys and rotatably actuates different elements to cut into occlusive material. Torque values, for example, may be measurable from the rotatable elements to differentiate between a free spinning element, an engaged element, and an element that is engaged with material the element should not be engaged with. These torque values (e.g., operational parameters) may be modified based on instructions transmitted from the processing circuitry to avoid the rotating element from damaging healthy tissue.

In one example, the catheter further includes at least one motor coupled with the cutting instrument, wherein the at least one motor is configured to impart rotational motion and/or axial motion, e.g., reciprocal axial motion, to the cutting instrument. In another example, the body includes a shaft, e.g., a cylindrical shaft, having a spiral shape surrounding the shaft. In an example, the body includes a central smooth surface configured to urge a cut portion of the target substance from a distal end of the body towards a proximal end of the body.

In some embodiments, establishing the baseline of one or more operational parameters comprises processing a selective data set that is representative of a heterogeneous population. Additionally, or alternatively, the at least one deviation from the established one or more baseline operational parameters of the separator instrument comprises at least one of a change in one or more of a rotational rate, a torque load, or a direction of rotation. The baseline of one or more operational parameters may be established by retrieving a data structure from memory corresponding to stored predefined expected ranges of the one or more operational parameters. A current operating state of the separator system is identified. A baseline value for the one or more operational parameters is selected based on the identified current operating state from the expected ranges of the one or more operational parameters. In some embodiments, the at least one deviation comprises interruptions, or pauses of operation, of the separator instrument. The at least one engagement condition of the separator instrument may comprise an engagement of the separator instrument with one or more of a saline solution, a blood solution, valve tissue, at least one blood clot, unusual tissue mass, foreign material, plaque, or a blood vessel.

In some embodiments, the one or more operational parameters comprises a torque. Additionally, or alternatively, establishing the baseline of the one or more operational parameters for the separator instrument comprises receiving a signal comprising torque information for a motorized separator, processing the signal to calculate a baseline torque in real-time. Identifying the at least one deviation from the established one or more baseline operational parameters of the separator instrument may comprise determining that one or more torque measurement values determined from the signal are anomalous relative to the baseline torque. Determining the at least one engagement condition of the separator instrument includes distinguishing the anomalous one or more torque measurements between being caused by an occlusion in a vasculature or being caused by something other than an occlusion.

In some embodiments, the signal is received from a sensor coupled to a motor of the motorized separator. Additionally, or alternatively, the torque information comprises at least one torque measurement value measured by the sensor at a sampling rate. The real-time baseline torque may be determined based on one or more of a current torque measurement value, a previously calculated baseline torque, or preclinically derived values. In some embodiments, the system stores in memory communicatively coupled to the processing circuitry a maximum value corresponding to the one or more operational values and a minimum value corresponding to the one or more operational parameters for each respective manufactured iteration of the system. The processing circuitry may utilize these values for additional processing. For example, the baseline of the one or more operational parameters is compared to the maximum value and the minimum value. Based on the comparing, a value corresponding to the baseline of the one or more operational parameters is determined to exceed the maximum value or the value is determined to be less than the minimum value. In response to the determining, the processing circuitry causes one or more of modifying the one or more operational parameters or terminating operation of the system without updating the baseline.

In some embodiments, the current torque measurement value and the previously calculated baseline torque are weighted based on a total number of torque measurements received from the signal. In some embodiments, a rate of change of torque values of the current torque measurement value is determined based on the sampling rate. A maximum calculated baseline torque and a minimum calculated baseline torque are computed by modifying the previously calculated baseline torque based on the rate of change of torque values. A range of updated baseline torque values are determined based on a comparison of the maximum calculated baseline torque and the minimum calculated baseline torque to the previously calculated baseline torque.

In some embodiments, the previously calculated baseline torque is weighted based on a first value calculated based on a tuning parameter and the total number of torque measurements values. The first value is calculated by subtracting the tuning parameter divided by the total number of torque measurement values from one and the real-time baseline torque may not be dynamically updated based on the current torque measurement value when the current torque measurement value is above an amplitude threshold. The amplitude threshold may be calculated based on the previously calculated baseline torque multiplied by a limit tuning parameter.

In some embodiments, the method incorporates determining a dynamic threshold based on the calculated baseline torque and a previously calculated baseline torque and determining the at least one torque measurement is anomalous relative to the baseline torque based on comparing a value of the at least one torque measurement to the dynamic threshold. Additionally, or alternative, the dynamic threshold comprises an upper bound and a lower bound. The upper bound is a multiplier of the previously calculated baseline torque, and the lower bound is a multiplier of a previously calculated baseline torque.

In some embodiments, the method incorporates determining the at least one torque measurement is anomalous based on whether the value of the at least one torque measurement is larger than the upper bound of the dynamic threshold or lower than the lower bound of the dynamic threshold. For two subsequent (e.g., consecutive or within a specified sampling period) measurements that exceed a bound of the dynamic threshold, a number of measurements in between are determined. The number of measurements in between is compared to a threshold. The threshold is determined based on the sampling rate of the signal and distinguishing the anomalous one or more torque measurements as being caused by the occlusion in the vasculature comprises identifying a pattern in the one or more torque measurement values associated with the occlusion in the vasculature.

In some embodiments, the something other than the occlusion comprises one or more of a change in direction of the motorized separator, a vessel wrapping, a valve, vessel wall, variance, noise, or an erroneous reading. Additionally, or alternatively, the anomalous one or more torque measurements may be determined to be caused by a vessel wrapping. In response to the determining, an operational parameter of the motorized separator may be changed.

In some embodiments, the disclosure is directed to a system for detecting different engagement conditions of a separator instrument. The system includes control circuitry communicatively coupled to the separator instrument, wherein the control circuitry is configured to transmit operational instructions to the separator instrument. Additionally, or alternatively, processing circuitry is communicatively coupled to the control circuitry, wherein the processing circuitry is configured to cause one or more circuitries to execute the methods and processes described herein. For example, one or more of the control circuitry or the process circuitry may be configured to receive and execute instructions as determined by processing a non-transitory computer-readable medium having non-transitory computer-readable instructions encoded thereon that, when executed by circuitry, cause the circuitry to execute one or more of the methods or processed of this disclosure.

BRIEF DESCRIPTIONS OF THE DRAWINGS

The above and other objects and advantages of the disclosure may be apparent upon consideration of the following detailed description, taken in conjunction with the accompanying drawings, in which:

FIG. 8 is a block diagram of an example process for detecting different engagement conditions, in accordance with some examples of the disclosure;

FIG. 9 is a block diagram of an example process for reviewing operational parameters of an instrument of this disclosure, in accordance with some examples of the disclosure;

FIG. 10 is a block diagram of an example process for calculating an amplitude threshold, in accordance with some examples of the disclosure;

FIG. 11 is a block diagram of an example process for determining an operational parameter measurement is anomalous relative to a baseline measurement of the operational parameter, in accordance with some examples of the disclosure;

FIG. 12 is a block diagram of an example process for using a bound of a dynamic threshold identify a number of measurements to process, in accordance with some examples of the disclosure; and FIG. 13 is a block diagram of an example process for determining a cause of an anomalous measurement, in accordance with some examples of the disclosure.

DETAILED DESCRIPTION

Figure 1:
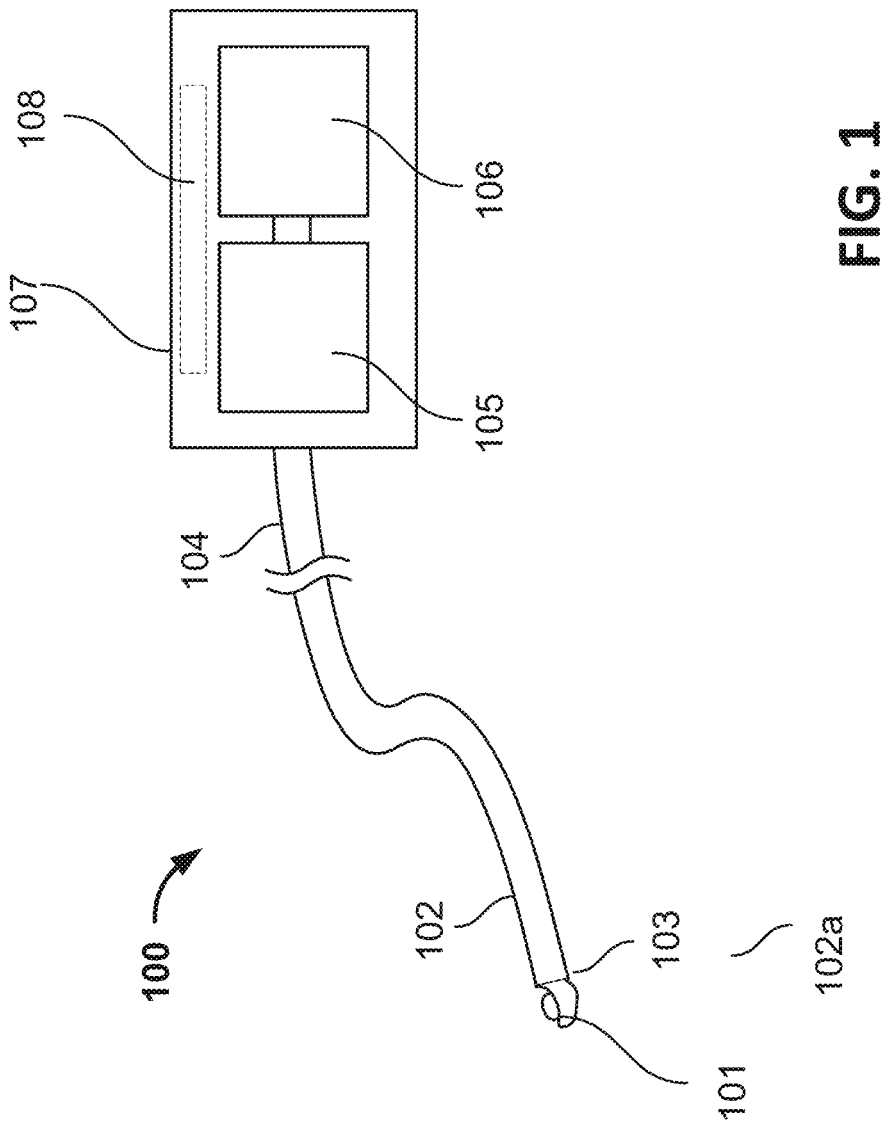
FIG. 1 shows a perspective view of a thrombectomy catheter system, in accordance with some embodiments of the disclosure.

Methods and systems are provided herein for modifying operation of a device that removes occlusive material based on a detection of an engagement condition between, for example, a separator instrument and the occlusive material.

Directional or positional terminology, such as "top," "bottom," "front," "back," "leading," "trailing," etc., is used with reference to the orientation of the figure(s) being described. Because components of examples of the present invention can be positioned in several different orientations, this terminology is used for purposes of illustration and is in no way limiting. Other combinations and/or modifications of the above-described structures, arrangements, applications, proportions, elements, materials, or components used in the practice of the present subject matter, in addition to those not specifically recited, may be varied or otherwise particularly adapted to specific environments, manufacturing specifications, design parameters, or other operating requirements without departing from the general principles of the same.

As used herein, the terms "distal" and "proximal" are understood as positional referents. Objects, elements, and components are "proximal to" or "distal to" one another on the system. "Proximal" refers to a direction toward the system controls and the operator along the path of the catheter system, and "distal" refers to the direction away from the system controls and the operator along the path of the catheter system toward or beyond a terminal end of the operating head.

As used herein, an aspiration source may refer to any device that supplies a negative pressure gradient. The source of negative pressure could be a vacuum pump, peristaltic pump, a progressive cavity pump, a diaphragm pump, a piston-based pump, a high-speed water jet disposed at a proper angle and orientation to create a favorable negative pressure gradient, or a simple syringe. All variations are understood to fall within the scope and spirit of the present invention.

As used herein, the term "occlusion" refers to both partial vessel occlusion and complete vessel occlusion. Examples of partial vessel occlusion include a vessel that is narrowed by hardened substances, such as plaque. Additionally, as used herein, the "complete" removal of an occlusion is understood as an effective removal of occlusive material, e.g., a thrombus. Occlusive material may escape removal, while a person having ordinary skill in the art would characterize the removal as complete in that the device has restored patency to the vessel.

As used herein, the term "catheter system" refers to a system configured to remove occlusive material from a body passage, such as a blood vessel. In the examples described herein, the catheter system has been exemplified as a thrombectomy catheter system. However, for the avoidance of doubt, the examples described herein are not limited to use as an instrument for the removal of thrombus from a body passage. Indeed, the examples described herein may be used for the removal of any appropriate occlusive material from a body passage, including, but not limited to, thrombus, atheroma, etc.

The methods and/or any instructions for performing any of the embodiments discussed herein may be encoded on computer-readable media. Computer-readable media includes any media capable of storing data. The computer-readable media may be transitory, including, but not limited to, propagating electrical or electromagnetic signals, or may be non-transitory including, but not limited to, volatile and non-volatile computer memory or storage devices such as a hard disk, floppy disk, USB drive, DVD, CD, media cards, register memory, processor caches, Random Access Memory (RAM), etc.

FIG. 1 illustrates a perspective view of a thrombectomy catheter system 100. System 100 includes specialized catheter or sheath catheter 102 attached to base unit 107 that houses motorized components (e.g., a controller, an aspiration pump, a clot collection container, etc.) that are operated by a user to effectuate working internal components (not visible in FIG. 1) of specialized catheter or sheath catheter 102 of system 100. A distal end 102a of the sheath catheter 102 is inserted into a vein, artery, or other passageway, advanced to a treatment site, and then deployed to mechanically disrupt, fragment, and aspirate a target substance(s) from the passageway. Helical cutting instrument 101 is disposed at a distal end of sheath catheter 102 and extends axially from an opening 103 at the distal end of sheath catheter 102. Helical cutting instrument 101 has a substantially spherical element having a rounded shape at its distal end serving as an atraumatic tip (as will be described in greater detail below) which reduces the risk that the passageway or the surface of a vessel or tissue will be damaged by the advancement of helical cutting instrument 101 through opening 103 of the sheath catheter 102. Opening 103 permits substance(s) from the patient's body to enter an aspiration lumen formed in the sheath catheter 102. The helical cutting instrument 101 also extends axially from the opening 103. A proximal end 104 of sheath catheter 102 is coupled to a motor 105 that provides rotational and/or reciprocal axial motions to internal components of sheath catheter 102. The proximal end 104 of sheath catheter 102 is in fluid communication with an aspiration source, such as pump 106, that provides a negative pressure gradient (e.g., vacuum suction) which draws and the target substance(s) through opening 103 and into the aspiration lumen of the sheath catheter 102. Other known aspiration sources may be used within the scope of this disclosure. Together, the negative pressure gradient and the mechanical fragmentation ensure the efficient and effective removal of substances from the body.

In alternative examples, system 100 may include more than one pump or valve in fluid communication with system 100. Such pumps and valves may provide or remove fluids in a way that alters the pressure within system 100. System 100 may be controlled by an ergonomically shaped handle (not illustrated in FIG. 1) that houses motor 105 and either houses or is in fluid contact with pump 106. This allows the user to easily control and manipulate system 100. System 100 also comprises processing and control circuitry 108. Processing and control circuitry 108 includes one or more components for receiving, processing, and transmitting data with respect to controlling and monitoring one or more of motor 105, catheter 102, or sensors (not shown) arranged throughout system 100 to collect data related to different components to determine if a modification of operation of one or more of motor 105 or catheter 102. For example, one form of operation data that could be used by processing and control circuitry 108 includes torque data which, when analyzed according to one or more processes and methods of this disclosure, can be correlated to an engagement or operational state of catheter 102. Depending on the engagement or operational state determined by processing and control circuitry 108, processing and control circuitry 108 may generate one or more instructions which, when executed, modify operation of system 100 to change the engagement or operational state.

Figure 2:
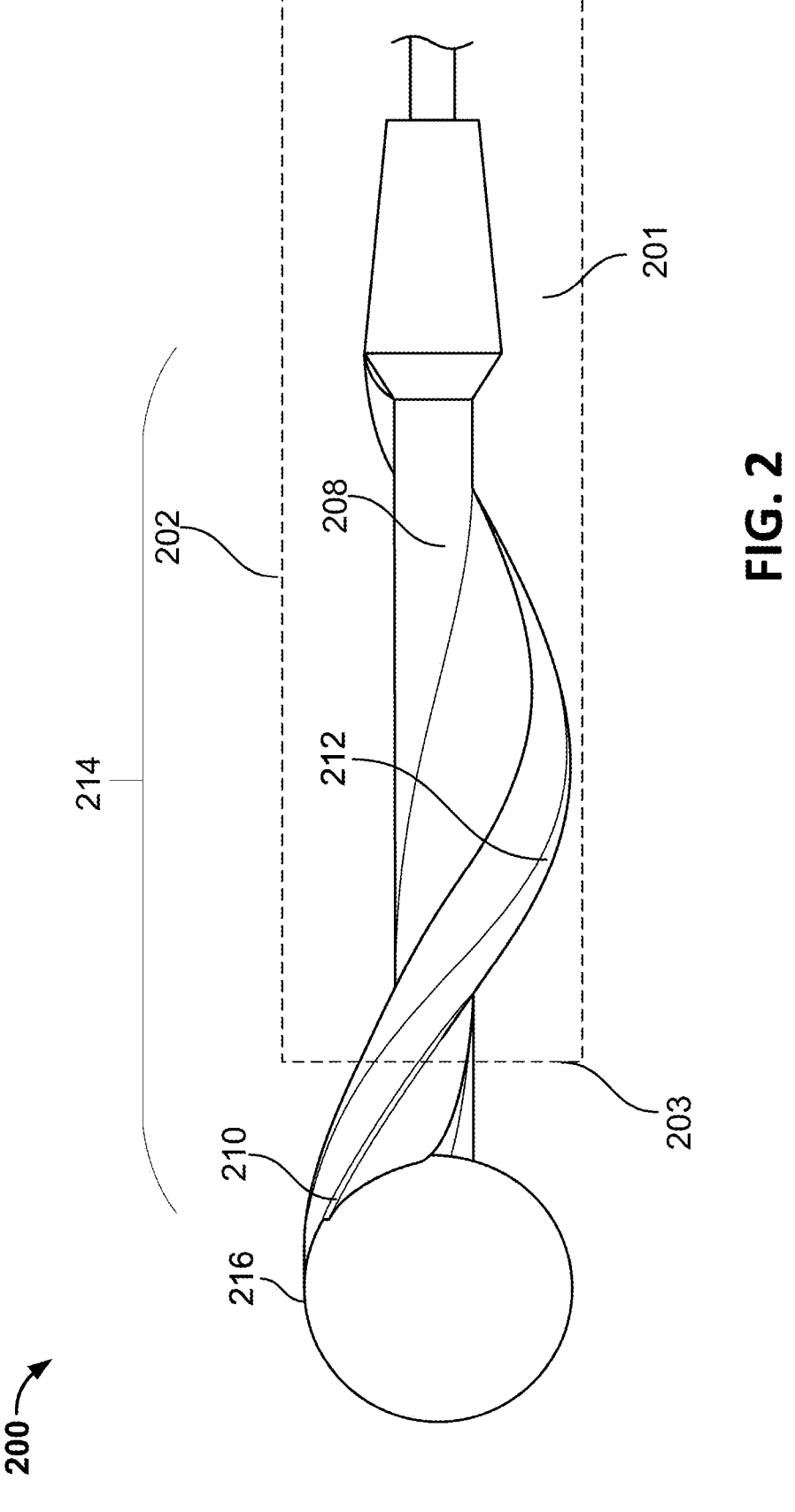
FIG. 2 shows a side detail view of a helical cutting instrument at a distal most segment of the thrombectomy catheter system, in accordance with some examples of the disclosure.

FIG. 2 shows a side detail view of a helical cutting instrument at a distal most segment of the thrombectomy catheter system, in accordance with some examples of the disclosure. The sheath catheter 202 of distal region 200 is shown as transparent (dashed lines) in order to facilitate an understanding of internal components. Distal region 200 of sheath catheter has an opening 203 from which the helical cutting instrument 201 axially extends from. Helical cutting instrument 201 includes a helical body 214 connected to a substantially spherical element 216 which serves as an atraumatic tip. The helical body 214 of helical cutting instrument 201 has a twisted, spiral shape, like a corkscrew, surrounding a central cylindrical shaft 208, as illustrated in FIG. 2. Helical body 214 includes a pair of edges 210 and 212 on the twisted spiral shape surrounding the central cylindrical shaft 208. In one example, the pair of edges 210 and 212 are each substantially sharpened, or otherwise configured to promote cutting of the target substance upon coming in contact. In another example, one of the edges 210, 212 is substantially sharpened while the other of the edges 210, 212 remains substantially blunt. In this configuration, when the helical body 214 is rotated, the substantially blunt edge is configured to gently pull on or draw in the target substance, while the substantially sharp edge is configured to slice or cut a small portion of the target substance upon coming in contact with the target substance.

Figure 3:
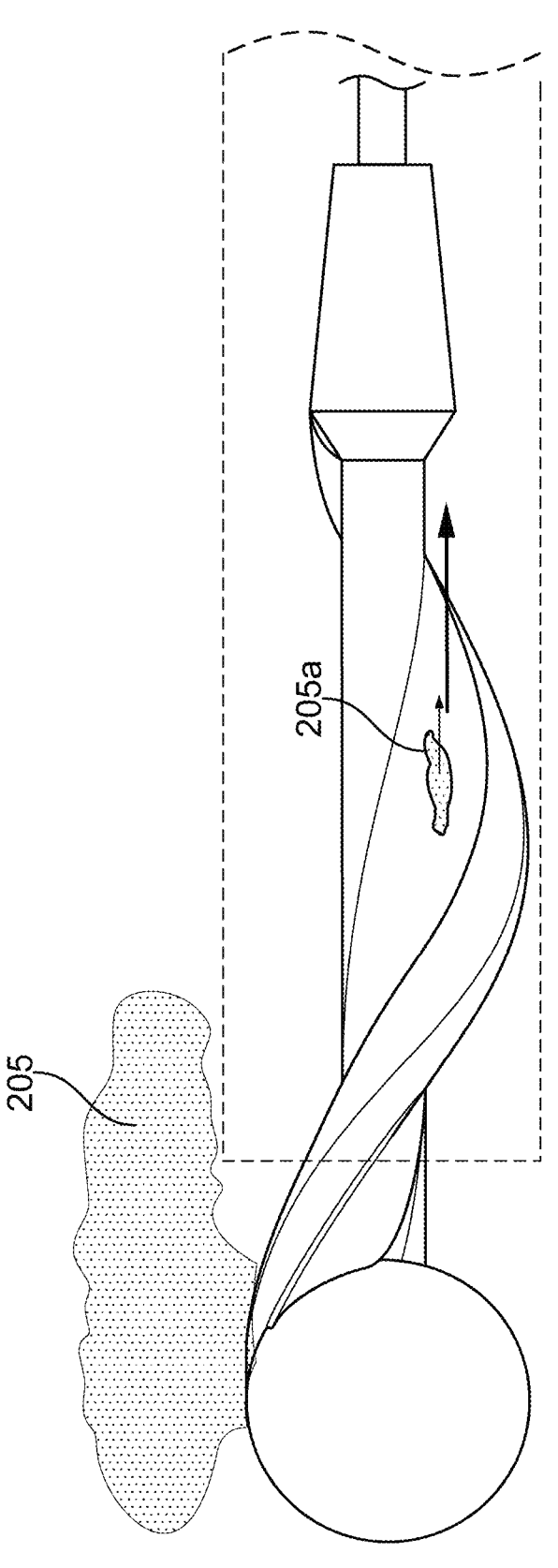
FIG. 3 shows a side, transparent, detail view of the helical cutting instrument in operation, in accordance with some examples of the disclosure.

FIG. 3 shows a side, transparent, detail view of the helical cutting instrument in operation, in accordance with some examples of the disclosure. As illustrated in FIG. 3, distal end of sheath catheter 202 is positioned proximal to a target substance 205. Motor 106 selectively provides rotational and/or axial motion to the helical cutting instrument 201 once sheath catheter 202 is positioned adjacent to the target substance to distally advance (usually while simultaneously rotating or rotationally oscillating) the helical cutting instrument 201 to extend from the distal end of sheath catheter 202. The substantially spherical element 216 serves as an atraumatic tip upon initial contact with the target substance 205. Specifically, the rounded, atraumatic distal substantially spherical element 216 allows for the safe advancement of the helical cutting instrument 201 through a diseased vessel or a targeted tissue.

In operation, once the substantially spherical element 216 of helical cutting instrument 201 is past the target substance 205, the target substance 205 comes in contact with the pair of rotating edges 210, 212 of helical body 214. As discussed above, in an example, the pair of edges 210 and 212 are each substantially sharpened and are configured to cut a piece of target substance 205 upon coming in contact as they rotate. Specifically, the target substance 205 is subjected to shearing forces by edges 210, 212, as the helical body 214 is being rotated or rotationally oscillated that cuts or slices the target substance 205. In another example, only one of the edges 210, 212 is substantially sharpened while the other of the edges 210, 212 remains substantially blunt. In this configuration, when the helical body 214 is rotated, the substantially blunt edge is configured to gently pull on or draw in the target substance 205, while the substantially sharp edge is configured to slice or cut a small portion 205a of the target substance 205 upon coming in contact.

The resulting fragments are then drawn into the lumen of sheath catheter 202 using a plurality of mechanisms working individually and/or cooperatively. Specifically, as further illustrated in FIG. 2E, as the double helical structure of helical body 214 is rotated, the distal end (i.e., the end connected to the substantially spherical element 216) scoops up the cut portion 205a of target substance 205 and moves it along the surface of helical body 214 towards a proximal end of the helical cutting instrument 201. For instance, in one example, the helical surface of the helical body provides a sliding channel for the cut portion 205a of the target substance 205 to be deposed from the distal section to the proximal section of the catheter 202. In another example, the helical surface of the helical body may include a grooved portion configured to provide a sliding channel for the cut portion 205a of the target substance 205. Moreover, the cut portion 205a of target substance 205 is further drawn into the lumen of sheath catheter 202 by an aspiration source (such as pump 106 in FIG. 1) that provides a negative pressure gradient within the lumen of sheath catheter 202. The cut portion 205a of target substance 205 are drawn into and through the sheath catheter lumen to a proximal region of sheath catheter 202 where they may be removed from the body of the patient.

In this way, the substances (e.g., fragments cut from tissues or clots) are broken up within the system and ingested, while aspiration ensures that minimal, if any, residual substance is permitted to escape evacuation. Once the target substance 205 or portion 205a thereof is inside the lumen of the sheath catheter 202, aspiration draws the substance through the lumen and into a collection chamber (not pictured).

A motor which axially advances and retracts the helical cutting instrument 201 along the lumen of the catheter and which may also simultaneously rotate or rotationally oscillate the helical cutting instrument 201 within the lumen of the catheter will typically be attached to a proximal end of the sheath catheter, as shown for example in FIG. 1, and may be housed in an ergonomically designed handle. The aperture may be formed in a separate structure at the distal end of the sheath catheter, such as in a separate housing. For example, the separate housing may be a metal or rigid polymeric tube having the aperture formed therein. In some examples, the helical cutting instrument 201 is a separate device from the sheath catheter and the helical cutting instrument 201 may be rotated as well as axially advanced and retracted separately and independently from the sheath catheter. The catheter may act as a sheath to the helical cutting instrument 201 in some examples.

While the example shown in FIG. 3 illustrates a helical cutting instrument 201 having double helix shaped edges, it is understood that the edges may take any appropriate form. Indeed, the cutting instrument 201 may comprises any appropriate number of edges, such as a single edge, or any multiple number of edges, e.g., depending on the configuration of the cutting instrument 201 and/or its intended operational purpose. In some examples, the cutting instrument may comprise at least one edge having a varying amount of curvature, e.g., the edge may comprise at least one straight portion (e.g., axially aligned portion) and at least one curved portion. In some examples, the edge may be a spiraled edge having a constant or varied pitch. In some examples, the radial height of the edge may be constant or varied along the length of the body 214. In some examples, the edge may extend radially outwards, e.g., perpendicularly, from a longitudinal axis of the body 214, e.g., for at least a portion of a length of the edge. In some examples, the edge may be raked forwards or backwards, e.g., inclined to or from, a longitudinal axis of the body 214, e.g., for at least a portion of a length of the edge. For the avoidance of doubt, the term "helical", when applied to the examples described herein, is not intended to be limiting and is used for the sake of example. Indeed, the present disclosure envisages that the benefits of the cutting instrument described herein may be achieved with any appropriately configured edge or edges of the cutting instrument 201.

In some embodiments, helical cutting instrument 201 is integrated into, or may be considered part of, a progressive cavity pump (hereinafter "PCP") assembly. A PCP is a positive displacement pump that may, for example, transfer fluid as a rotor is turned. A volumetric flow rate of fluid transfer is proportional to a potentially bidirectional rotational rate of the rotor, assuming reduced levels of shearing being caused by the rotor as applied to the fluid being pumped through the assembly. The rotor of the PCP may, for example, incorporate helical cutting instrument 201 to cause the bidirectional rotation within a fluid interfacing with helical cutting instrument 201. Ideally, helical cutting instrument 201 can be controlled, or actuated, via controls of PCP assembly to ensure minimal variation in net fluid flow in a desired direction (e.g., pulling fluid or other displaced material out of an occluded region of a vascular region).

Figure 4:
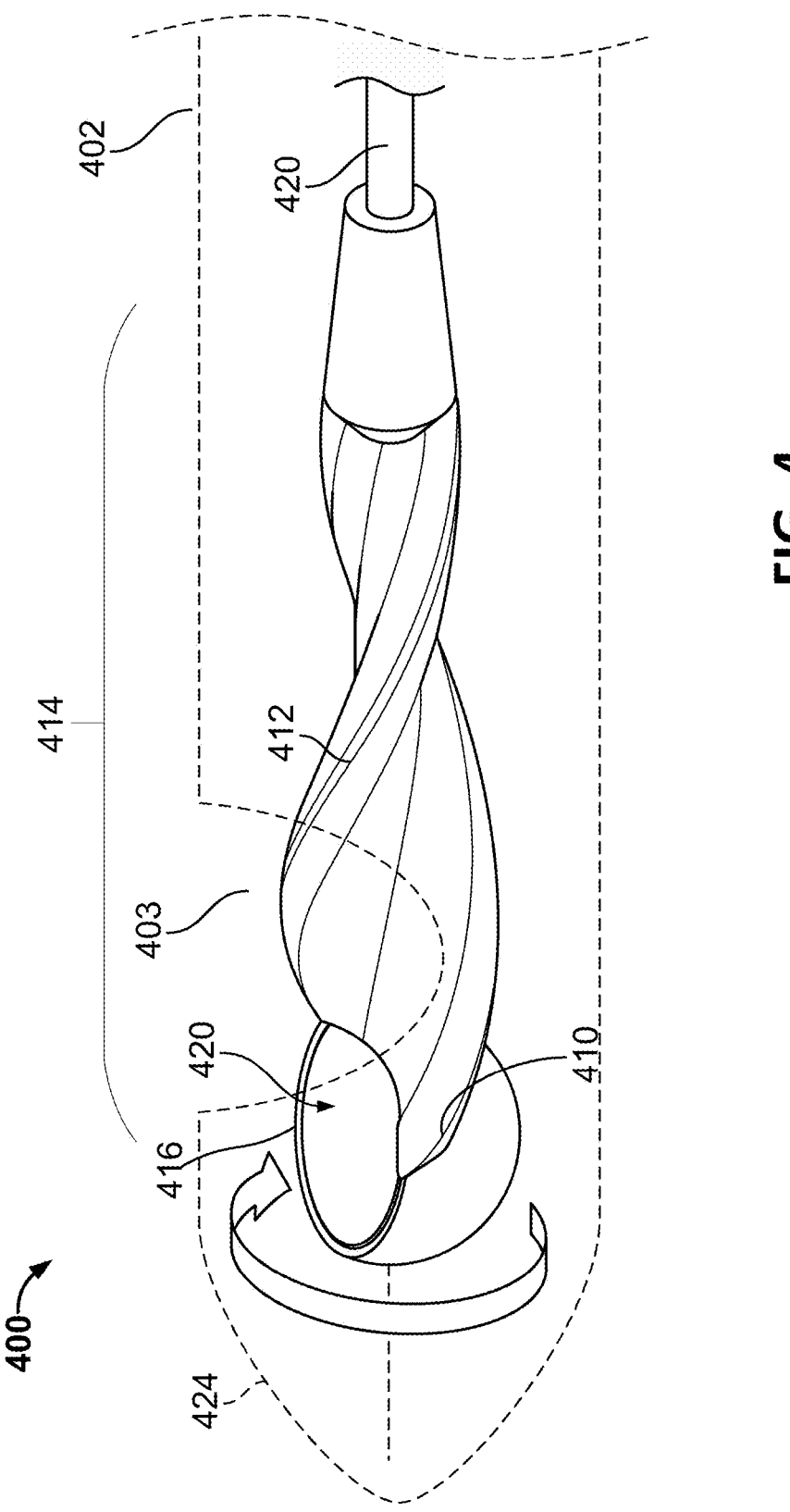
FIG. 4 shows a side detail view of another implementation of the helical cutting instrument, in accordance with some examples of the disclosure.

FIG. 4 shows a side detail view of another implementation of the helical cutting instrument, in accordance with some examples of the disclosure. Helical cutting instrument 401 of FIG. 4 includes a substantially spherical element 416 connected to a helical body 414. The operation of helical body 414 is similar to that of helical body 214 discussed above in connection with FIGS. 2 and 3. The substantially spherical element 416 of helical cutting instrument 401 differs from substantially spherical element 216 of helical cutting instrument 201 in that the substantially spherical element 416 includes a scooped-out portion 420. In an example, an edge portion of the scooped-out portion 420 is substantially sharpened or otherwise configured to promote cutting of the target substance as the substantially spherical element 416 comes in contact with the target substance (while simultaneously being rotated or rotationally and laterally oscillated). Moreover, as further illustrated in FIG. 4, the scooped-out portion 420 is designed to open into the helical body 414 of the helical cutting instrument 401. This allows for any sliced or cut portions of the target substance to be moved proximally along the helical body 414 (e.g., via a central channel or central surface, which may be substantially flat and/or smooth) by leveraging the helical shape of the helical body 414.

Moreover, as illustrated in FIG. 4, in some examples, sheath catheter 402 includes an aperture 403 and an atraumatic distal tip 424, which may be softer/more flexible relative to the remainder of the sheath catheter 402. The soft, atraumatic distal tip 424 allows for the safe advancement of the device through the diseased vessel. A substantially sharpened edge of the scooped-out portion 420 is typically serrated or otherwise configured to promote cutting of the target substance as the helical cutting instrument 401 is advanced (and optionally rotated and/or rotationally oscillated). The substantially sharpened edge of the scooped-out portion 420 is configured to promote shearing of the excised portion of the target substance from the remaining mass of target substance as the leading edge engages the target substance.

The aperture 403 is typically formed as a "side window" in the distal region of the sheath catheter 402, and the helical cutting instrument 401 may be advanced and retracted to adjust the size of a gap between the cutting body and the distal end of the window. Aspiration pulls the target substance, such as clot material, to the open window, and the rotating helical cutting instrument 401 fragments the clot as it enters the window. A motor which rotates or rotationally oscillates the helical cutting instrument 401 will typically be attached to a proximal end of the sheath catheter, as shown for example in FIG. 1, and may be housed in an ergonomically designed handle. The aperture may be formed in a separate structure at the distal end of the sheath catheter, such as in a separate housing. For example, the separate housing may be a metal or rigid polymeric tube having the aperture formed therein. In some examples, both the sheath catheter and the helical cutting instrument are substantially flexible and pliable.

Figures 5A, 5B:
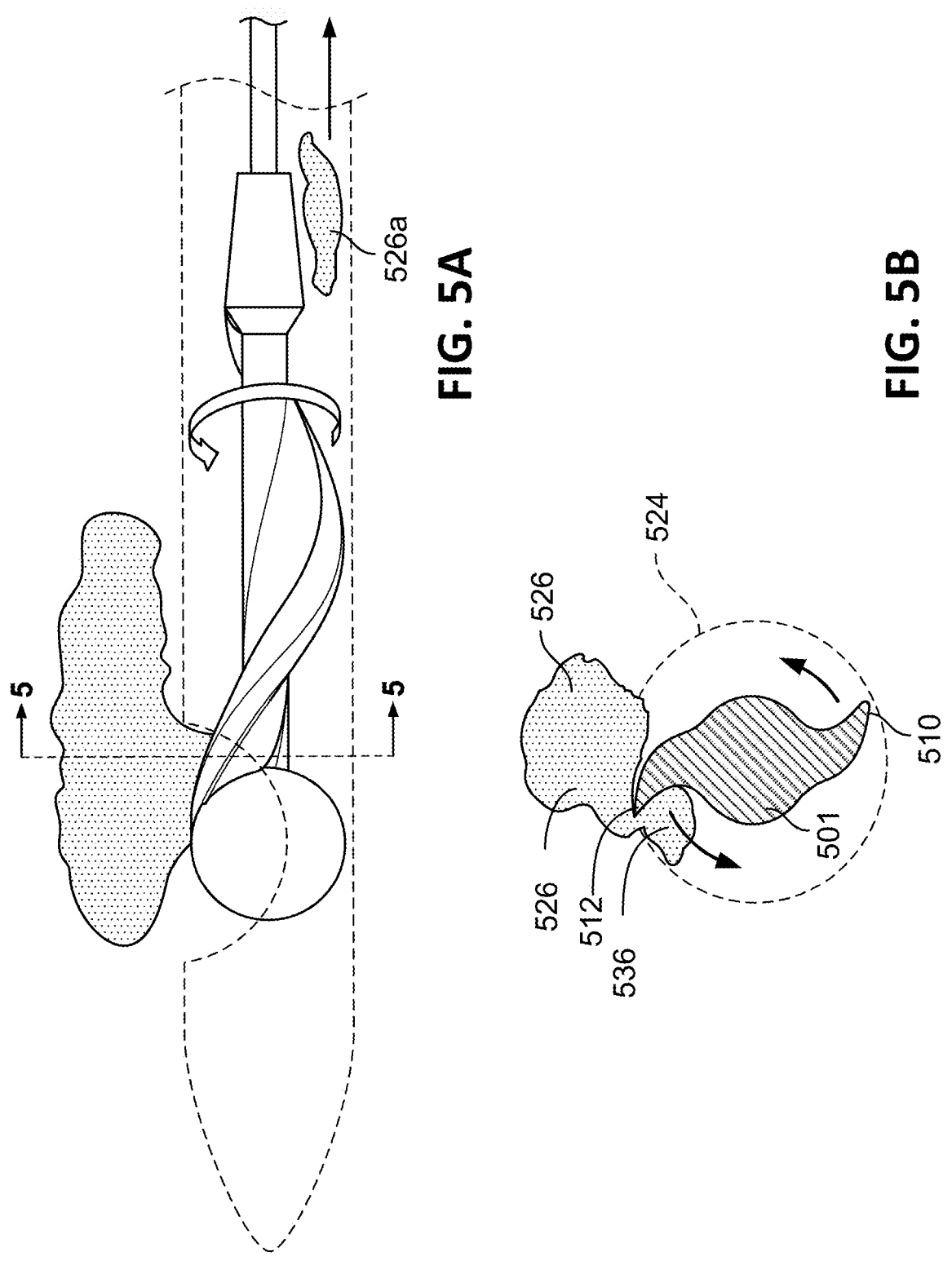
FIG. 5A shows a side, transparent, detail view of the helical cutting instrument of FIG. 4 in operation, in accordance with some examples of the disclosure.
FIG. 5B shows a cross-section of the helical cutting instrument of FIG. 4, in accordance with some examples of the disclosure.

FIG. 5A illustrates system 500 at a fourth point in time, when system 500 is in a configuration a rotation of the helical cutting instrument. As shown in FIG. 5A, the discreet and relatively uniform slicing or shearing of the target substance due to the rotational shearing force applied on the target substance. The axial and rotational motion of the helical cutting instrument 501, which ultimately places the cutting edge of the scooped-out portion 520 and the cutting edges 510, 512 of the helical body 514 into contact with the target substance 526, causes the shearing or slicing of target substance 526.

As the helical cutting instrument 501 moves axially while simultaneously rotating or rotationally oscillating, target substance 526 may be sliced into smaller portions. This slicing creates a discreet and relatively uniform fragment, which is then immediately aspirated, in part by the helical structure of the helical body 514. As the helical cutting instrument 501 slices or cuts the target substance, the cut portion generated is aspirated along the helical body 514 (e.g., by way of a channel surface of the helical body) in a proximal direction. The relatively uniform fragments 526a are then further aspirated in a proximal direction (indicated by the arrow) within the sheath catheter's lumen. This fragmentation occurs within the sheath catheter's lumen, and thereby reduces the risk of clot fragment dispersal within the patient's vasculature.

FIG. 5B shows a cross-section of the helical cutting instrument of FIG. 5A along line 5-5, in accordance with some examples of the disclosure. As illustrated in FIG. 5B, as the helical cutting instrument 501 is rotated or rotationally oscillated within a lumen of sheath catheter 524, a shearing force is applied on the target substance 526 by edges 510, 512 of the helical cutting instrument 501. The shearing force applied by the edges 510, 512 of the helical cutting instrument 501 causes target substance 526 to be sliced. This slicing creates a discreet and relatively uniform fragment 536, which is then aspirated along the helical body of the helical cutting instrument 501 in a proximal direction.

Although FIG. 5B shows an anti-clockwise rotation of the helical cutting instrument 501, in other examples, the helical cutting instrument 501 can be rotated in a clockwise direction. In one example, edge 510 of the helical cutting instrument 501 is substantially blunt while edge 512 of the helical cutting instrument 501 is substantially sharpened, or otherwise configured to promote cutting of the target substance 526. When the edge 510 first comes into contact with the target substance 526, instead of cutting or slicing the target substance, edge 501 pulls onto a fragment (e.g., fragment 536) of the target substance 526 into the lumen of the sheath catheter. Continued rotation of the helical cutting instrument 501 causes substantially sharpened edge 512 to come into contact with the fragment 536 which then proceeds to cut or slice that fragment. In this manner, the two different edges 510, 512 work together to slice small discreet portions of the target substance 526, while preventing damage to the blood vessels.

Figure 6:
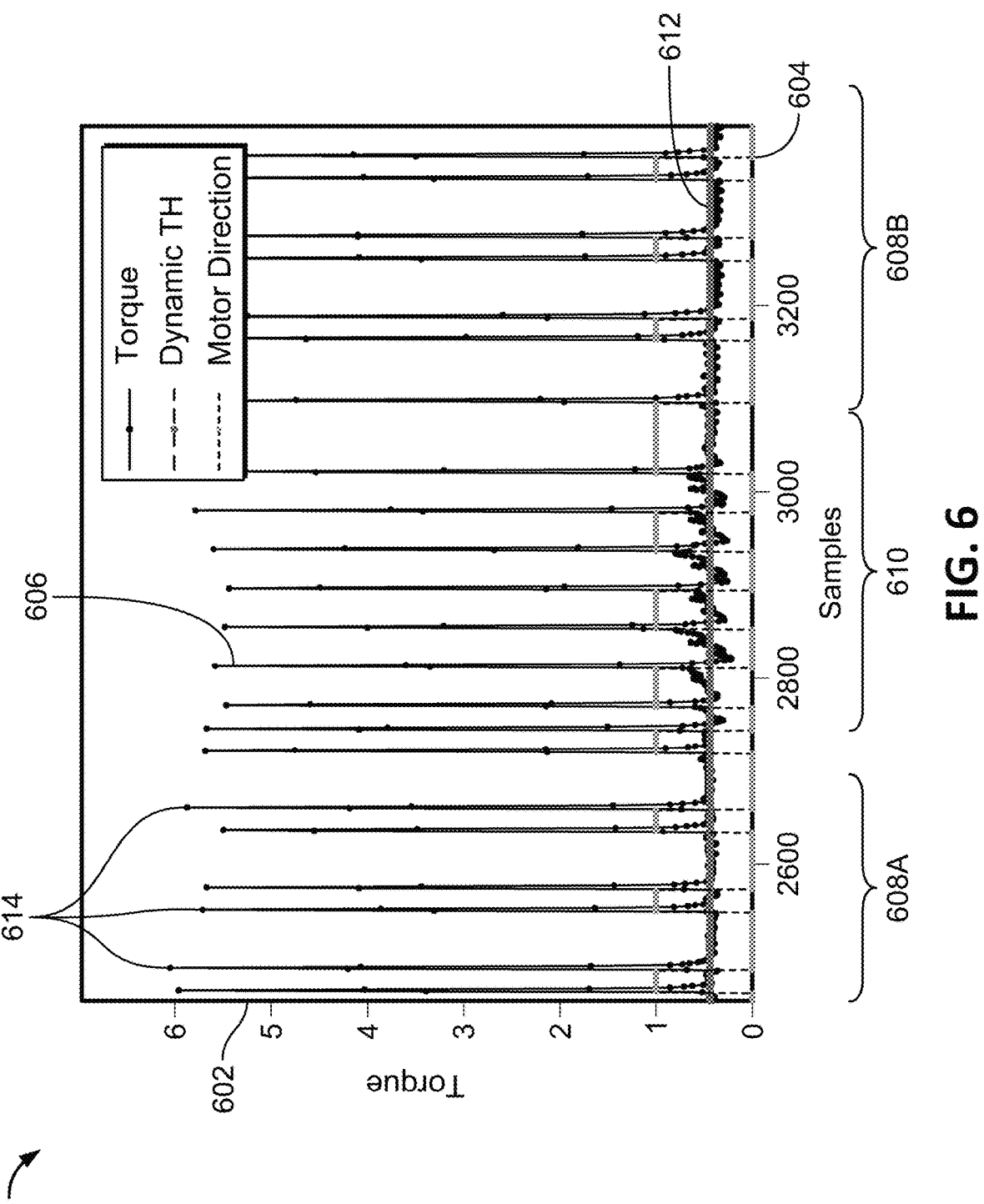
FIG. 6 depicts an example graph of data characterizing an operational parameter as compared to a baseline of the operational parameter, in accordance with some examples of the disclosure.

FIG. 6 depicts graph 600 of data characterizing an operational parameter as compared to a baseline of the operational parameter, in accordance with some examples of the disclosure. Graph 600 represents data collected with respect to a torque measurement as a separator instrument engages one or more of occlusive material or other elements within a vascular system. The data of graph 600 may be used in whole or in part to execute any or all of process 800 of FIG. 8, process 900 of FIG. 9, process 1000 of FIG. 10, process 1100 of FIG. 11, process 1200 of FIG. 12, and process 1300 of FIG. 13. Graph 600 may be used characterize operation of one or more elements or components shown in or described in reference to FIGS. 1-5B.

Graph 600 includes vertical axis 602, horizontal axis 604, and separator torque data 606. Separator torque data 606 includes normal operation samples 608A and 608B as well as wrap condition operation samples 610. Dynamic threshold 612 provides a baseline for expected operational deviations and as shown in wrap condition operation samples 610, deviations from dynamic threshold 612 corresponds to the separator instruction being intertwined with tissue of the vascular system being treated.

As part of executing the processes characterized by FIGS. 8-13, the data represented via graph 600. As shown by separator torque data 606, the motor torque of the motor driving the separator generates peaks 614 each time a change of direction of the motor occurs. Although not explicitly shown via graph 600, separator torque data 606 may include unwanted noise in the recorded data based on one or more of processing rate or abrupt changes in engagement status of the separator. Additionally, dynamic threshold 612 is expected to be different based on one or more of a different patient having a procedure done using the separator or a different piece of hardware (e.g., motor and separator combination) as there are physiological differences between patients as there are manufacturing tolerances with devices. Dynamic threshold 612 is not, however, affected by a wrap situation as change in values depicted in wrap condition operation samples 610 may be based on a rotation rate of the device removing occlusive material. In some embodiments, a wrap condition may be detected based on variation in cyclical responses of the device (e.g., based on periodic direction changes with varying device responses) and does not affect the baseline in a manner that a different patient or different device would modify dynamic threshold 612. The calculations related to establishing dynamic threshold 612 is intentionally set such that a baseline is not modified in response to detection of a wrap condition. Conversely, dynamic threshold 612 is calculated and established to verify wrap conditions are occurring and dynamic threshold 612 is presented based on intelligent consideration of varying device level variations before a particular device experiences a wrap condition.

In some embodiments, the system stores in memory communicatively coupled to the processing circuitry a maximum value corresponding to the one or more operational values and a minimum value corresponding to the one or more operational parameters for each respective manufactured iteration of the system. The processing circuitry may utilize these values for additional processing. For example, the baseline of the one or more operational parameters is compared to the maximum value and the minimum value. Based on the comparing, a value corresponding to the baseline of the one or more operational parameters is determined to exceed the maximum value or the value is determined to be less than the minimum value. In response to the determining, the processing circuitry causes one or more of modifying the one or more operational parameters or terminating operation of the system without updating the baseline.

To obtain a baseline for using to identify an engagement status, tracking baselines for different patients that are not affected by the unwanted peaks, noise, and wrapping, described herein is an algorithm that rapidly learns a patient and device baseline towards the beginning of an operation cycle to ensure adjustment or modification of operation of the device in a particular patient prevents or avoids a wrapping condition (e.g., as characterized by the data of wrap condition operation samples 610). Separator torque data 606 is represented from a computation perspective as $x(i)$, i=1, 2, . . . , N, where N equals the total number of data samples (e.g., as defined by a sampling rate of a sensor associated with one or more of the motor or the separator instrument). The dynamic threshold (e.g., as represented by dynamic threshold 612) computationally is represented as the function DT(i), where i=1, 2, . . . , N corresponding to the computation of the threshold based on a first data sample, a second data sample, and up to N data samples. In some embodiments, an initial value of dynamic threshold 612 (e.g., based on a scale of vertical axis 602) may be computed via the function DT(i) to provide more complete input to subsequent iterations of the computations performed via function DT(i), thereby improving accuracy of the magnitude of dynamic threshold 612 with less repeated computations.

To provide an example of a computed learning rate of dynamic threshold 612, the value of dynamic threshold 612 is represented by the formula below, wherein N is the number of samples utilized in the computation:

$$\lambda(i) = 1 - (\tau/i), i = 2, 3 \ldots , N$$

The learning rate is then fed back into the dynamic threshold function as exemplified below:

$$DT(i) = \lambda(i) * DT(i - 1) + (1 - \lambda(i)) * x(i)$$

In some embodiments, a time constant (e.g., a period of time which captures a particular number of data samples) may be applied to one or more of the above referenced formulas to modify the weight of a currently computed value of the dynamic threshold as it is used in a computation for a predictive or subsequent dynamic threshold. The time constant may be represented by the character t, and may also be applied to newer data samples (e.g., where the initially computed dynamic threshold was based on a one data sample and there is significantly more subsequent data samples available which impact the dynamic threshold value with more significance than the first data sample). The value of t may be a scalar value, such as 1, to avoid significant impact of weighting different samples of data. In some embodiments, the value of t may be adjusted to any suitable value depending on the calibration settings of a device based on one or more of manufacturing tolerances or specific patient characteristics.

To avoid the peaks from motor direction change and noise affecting the dynamic threshold, computer readable instructions may incorporate logic to modify the dynamic threshold function to the below:

$$DT(i) = \lambda(i) * DT(i - 1) + (1 - \lambda(i)) * x(i),$$

$$\text{when } x(i) < \eta * DT(i - 1), i = 2, 3, \ldots , N.$$

By modifying the value, or range of values, corresponding to n (e.g., a noise limiting parameter), this updated formula provides a built-in processing loop for computing means to minimize the effect of noise in the data and wrap situation data on the dynamic threshold. For example, to determine if the wrap occurs or not, the number of data samples that are larger than the dynamic threshold is computed based on the below relationship:

$$\text{If } x(i) > \eta * DT(i - 1), DT(i) = DT(i - 1), i = 2, 3, \ldots , N.$$

For each data point, if $x(i) > 2 * DT(i)$, i=2, 3, . . . , N, then a value that exceeds the dynamic threshold is denoted as $\delta(k) = i$, wherein i is updated based on the scalar number of data points above the threshold within a group of data samples. In some embodiments, the data points may have significant differences in values when exceeding the dynamic threshold (e.g., as represented by the variation in values of peaks 608). When two values are far from each other (e.g., if $\delta(k) - \delta(k-1) > 5$ for a sampling rate equaling to 100 Hz), then a reset of the value of $\delta$ occurs to ensure the data points exceeding the threshold are correctly fed into a corrective algorithm for operating the separator.

In some embodiments, torque values that are below the dynamic threshold are also considered to improve detection of wrap conditions. For example, the below relationship may be employed to provide insight as to when deviations below the threshold are to be considered:

$$\text{when } x(i) < 0.5 * DT(i - 1), i = 2, 3, \ldots , N$$

Although wrap detection is most often detected based on a determination that a certain number of data points within a sampling period or sampling cycle exceed the dynamic threshold, there is evidence that torque values that are below the dynamic threshold are also indicative of a wrap condition as shown via wrap condition operation samples 610. As a result, by using data from both sides of the dynamic threshold, a wrap condition can be identified earlier than if only one set of data is utilized and modification of operation of the separator can be achieved prior to causing any patient level issues.

Figure 7:
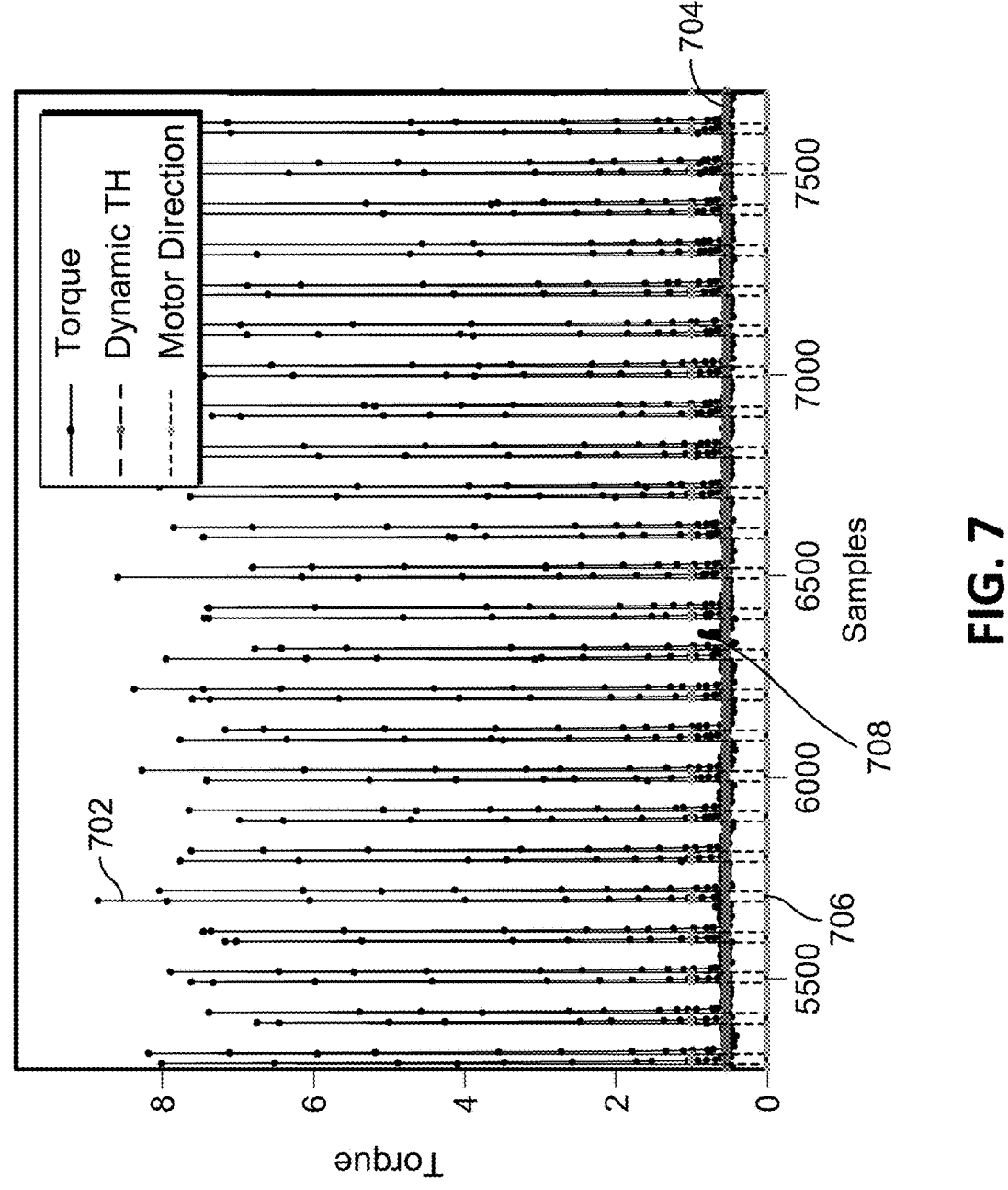
FIG. 7 depicts an example graph of data characterizing an operational parameter when an instrument of this disclosure interfaces with an occlusion, in accordance with some examples of the disclosure.

FIG. 7 depicts graph 700 of data characterizing an operational parameter when an instrument of this disclosure interfaces with an occlusion, in accordance with some examples of the disclosure. Graph 700 represents data collected with respect to a torque measurement as a separator instrument engages one or more of occlusive material or other elements within a vascular system. The data of graph 700 may be used in whole or in part to execute any or all of process 800 of FIG. 8, process 900 of FIG. 9, process 1000 of FIG. 10, process 1100 of FIG. 11, process 1200 of FIG. 12, and process 1300 of FIG. 13. Graph 700 may be used to characterize operation of one or more elements or components shown in or described in reference to FIGS. 1-5B.

Graph 700, in contrast to Graph 600, represents a data sample where a wrap condition is not realized (e.g., based on adjustments or modifications to operational parameters of the separator instrument or motor). Data profile 702 represents data samples of a motor torque and data profile 706 represents a step function that characterizes direction of a motor (e.g., to interface with an remove an occlusion). Dynamic threshold 704 is computed based on the algorithms described in reference to FIG. 6 and may be updated based on changes in data profile 702 (e.g., in the event data profile 702 changes from a profile similar to normal operation samples 608A and 608B to a profile similar to wrap condition operation samples 610). Presence of occlusive material is detected based on data profile 702. For example, a clot is identified based on the presence of data deviation 708 which indicates an increase in torque over a number of data samples.

FIG. 8 is a block diagram of process 800 for detecting different engagement conditions, in accordance with some examples of the disclosure. Process 800 may be executed by processing and control circuitry 108 of FIG. 1. Additionally, or alternatively, process 800 may be executed, in whole or in part, as part of or contemporaneous to any or all of process 900 of FIG. 9, process 1000 of FIG. 10, process 1100 of FIG. 11, process 1200 of FIG. 12, and process 1300 of FIG. 13. Data as characterized by one or more of graph 600 of FIG. 6 or graph 700 of FIG. 7 may be utilized as part of the execution of process 800.

At process block 802, a baseline of one or more operation parameters for the separator instrument are determined. The baseline is characterized via stored predefined expected ranges that characterize healthy blood that is without one or more of clots or occlusions. In some embodiments, as characterized by callout 802A, a selective data set that is representative of a heterogeneous population is processed. At process block 804, at least one deviation from the established one or more baseline operation parameters of the separator instrument are identified. As characterized by callout 804A, the deviation from the baseline of the one or more operation parameters includes one or more of a change in one or more of a rotational rate, a torque load, or a direction or rotation. Additionally, or alternatively, as characterized by callout 804B, the deviation from the baseline of the one or more operation parameters includes interruptions, or pauses of operation, of the separator instrument. At process block 806, the identified at least one deviation is determined to correspond to at least one engagement condition of the separator instrument. As characterized by callout 806A, the engagement condition includes one or more of an engagement of the separator instrument with one or more of a saline solution, a blood solution, valve tissue, at least one blood clot, unusual tissue mass, foreign material, plaque, or a blood vessel. At process block 808, an action is caused to be performed based on the determining (e.g., modifying torque or speed of a rotating component engaged with occlusive material, or modifying a distance which the separator is extended).

FIG. 9 is a block diagram of process 900 for reviewing operational parameters of an instrument of this disclosure, in accordance with some examples of the disclosure. Process 900 may be executed by processing and control circuitry 108 of FIG. 1. Additionally, or alternatively, process 900 may be executed, in whole or in part, as part of or contemporaneous to any or all of process 800 of FIG. 8, process 1000 of FIG. 10, process 1100 of FIG. 11, process 1200 of FIG. 12, and process 1300 of FIG. 13. Data as characterized by one or more of graph 600 of FIG. 6 or graph 700 of FIG. 7 may be utilized as part of the execution of process 900.

At process block 902, the operational parameter comprises a torque. At process block 904, a signal comprising torque information for a motorized separator is received. As characterized by callout 904A, the signal may be from a sensor coupled to a motor of the motorized separator. If the torque information is from the sensor, the process block 904B is used to determine the torque information comprises at least one torque measurement value measured by the sensor at a sampling rate. As characterized by callout 904C, in some embodiments, real-time baseline torque is not dynamically updated based on the current torque measurement value when the current torque measurement value is above an amplitude threshold. At process block 906, the signal is processed to calculate a baseline torque in real time. In some embodiments, process block 908 is employed immediately after process block 906. In other embodiments, process block 906A-906D may be employed after process block 906 and before process block 908. At process block 906A, the real-time baseline torque is determined based on one or more of a current torque measurement value, a previously calculated baseline torque, or preclinically derived values (e.g., stored in memory or communicatively accessible via a server). At process block 906B, the current torque measurement value and the previously calculated baseline torque is weighted based on a total number of torque measurement values received from the signal. At process block 906C, the previously calculated baseline torque is weighted based on a first value calculated based on a tuning parameter and the total number of torque measurement values. At process block 906D, the first value is calculated by subtracting the tuning parameter divided by the total number of torque measurement values from an integer with a value of one. At process block 908, the one or more torque measurement values determined from the signal are determined to be anomalous relative to the baseline torque. At process block 910, the anomalous one or more torque measurements are distinguished between being caused by an occlusion in a vasculature or being caused by something other than an occlusion (e.g., a mechanical failure of part of the system).

FIG. 10 is a block diagram of process 1000 for calculating an amplitude threshold, in accordance with some examples of the disclosure. Process 1000 may be executed by processing and control circuitry 108 of FIG. 1. Additionally, or alternatively, process 1000 may be executed, in whole or in part, as part of or contemporaneous to any or all of process 800 of FIG. 8, process 900 of FIG. 9, process 1100 of FIG. 11, process 1200 of FIG. 12, and process 1300 of FIG. 13.

Data as characterized by one or more of graph 600 of FIG. 6 or graph 700 of FIG. 7 may be utilized as part of the execution of process 1000.

Decision block 1002 is utilized to determine whether the real-time baseline torque is dynamically updated based on the current torque measurement value when the current torque measurement value is above an amplitude threshold. If the real-time baseline torque is dynamically updated based on the current torque measurement value when the current torque measurement value is above an amplitude threshold (YES at 1002), the process block 908 of process 900 is utilized for further processing. If the real-time baseline torque is not dynamically updated based on the current torque measurement value when the current torque measurement value is above an amplitude threshold (NO at 1002), the process block 1004 is utilized for further processing. At process block 1004, the amplitude threshold is calculated based on the previously calculated baseline torque multiplied by a limit tuning parameter (e.g., as provided, identified, or determined based on one or more of system capabilities, system calibrations, or encoded operational limits).

FIG. 11 is a block diagram of process 1100 for determining an operational parameter measurement is anomalous relative to a baseline measurement of the operational parameter, in accordance with some examples of the disclosure. Process 1100 may be executed by processing and control circuitry 108 of FIG. 1. Additionally, or alternatively, process 1100 may be executed, in whole or in part, as part of or contemporaneous to any or all of process 800 of FIG. 8, process 900 of FIG. 9, process 1000 of FIG. 10, process 1200 of FIG. 12, and process 1300 of FIG. 13. Data as characterized by one or more of graph 600 of FIG. 6 or graph 700 of FIG. 7 may be utilized as part of the execution of process 1100.

Process 1100 is utilized in the event process 900 progresses to process block 904 based on one or more conditions described in reference to FIG. 9. At process block 1102, a dynamic threshold is determined based on a calculated baseline torque and a previously calculated baseline torque. As characterized by callout 1102A, the dynamic threshold may comprise an upper bound and a lower bound. Callout 1102B clarifies the upper bound may be a multiplier of the previously calculated baseline torque. Callout 1102C clarifies the lower bound is a multiplier of a previously calculated baseline torque. At process block 1104, the at least one torque measure is determined to be anomalous relative to the baseline torque based on comparing a value of the at least one torque measure to the dynamic threshold.

FIG. 12 is a block diagram process 1200 for using a bound of a dynamic threshold identify a number of measurements to process, in accordance with some examples of the disclosure. Process 1200 may be executed by processing and control circuitry 108 of FIG. 1. Additionally, or alternatively, process 1200 may be executed, in whole or in part, as part of or contemporaneous to any or all of process 800 of FIG. 8, process 900 of FIG. 9, process 1000 of FIG. 10, process 1100 of FIG. 11, and process 1300 of FIG. 13. Data as characterized by one or more of graph 600 of FIG. 6 or graph 700 of FIG. 7 may be utilized as part of the execution of process 1200.

At process block 1202, the at least one torque measure is determined to be anomalous based on whether the value of the at least one torque measurement is larger than the upper bound of the dynamic threshold or lower than the lower bound of the dynamic threshold (e.g., based on the upper and lower bound characterized by callouts 1102B and 1102C of FIG. 11). At process block 1204, a number of measurements are determined for two subsequent measurements that exceed a bound of the dynamic threshold, where the number of measurements correspond to values in between the two subsequent measurements. At process block 1206, the number of measures in between are compared to a threshold. As characterized by callout 1206A, the threshold is determined based on the sampling rate of the signal (e.g., a signal communicating torque data as measured by a torque sensor in the system).

FIG. 13 is a block diagram of process 1300 for determining a cause of an anomalous measurement. Process 1300 may be executed by processing and control circuitry 108 of FIG. 1. Additionally, or alternatively, process 1300 may be executed, in whole or in part, as part of or contemporaneous to any or all of process 800 of FIG. 8, process 900 of FIG. 9, process 1000 of FIG. 10, process 1100 of FIG. 11, and process 1200 of FIG. 12. Data as characterized by one or more of graph 600 of FIG. 6 or graph 700 of FIG. 7 may be utilized as part of the execution of process 1300.

Process 1300 is utilized in the event process 900 progresses to process block 910 based on one or more conditions described in reference to FIG. 9. As characterized by callout 910A, a pattern in the one or more torque measurement values associated with the occlusion in the vasculature is identified and is therefore used to distinguish, via process block 910, an anomalous one or more torque measurements as being causing by an occlusion instead of something other than an occlusion. Additionally, or alternative, as characterized by 910B, the something other than the occlusion is distinguished from the occlusion, via process block 910, as comprising one or more of a change in direction of the motorized separator, a vessel wrapping, a valve, vessel wall, variance, noise, or an erroneous reading. Each of the conditions affiliated with something other than the occlusion is based on one or more stored or communicatively accessible data ranges or patterns characterized for the system to decide a corrective action in response to certain data ranges or patterns. At process block 1302, the anomalous one or more torque measurements are determined to be caused by a vessel wrapping. At process block 1304, an operational parameter of the motorized separator is changed in response to the determining (e.g., modifying torque or speed of a rotating component engaged with occlusive material, or modifying a distance which the separator is extended).

The systems and processes discussed above are intended to be illustrative and not limiting. One skilled in the art would appreciate that the actions of the processes discussed herein may be omitted, modified, combined, and/or rearranged, and any additional actions may be performed without departing from the scope of the invention. More generally, the above disclosure is meant to be exemplary and not limiting. Only the claims that follow are meant to set bounds as to what the present disclosure includes. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

While some portions of this disclosure may refer to "convention" or examples, any such reference is merely to provide context to the instant disclosure and does not form any admission as to what constitutes the state of the art.

What is claimed is:

1. A method for detecting different engagement conditions of a separator instrument of a system comprising the separator instrument, the method comprising:

establishing, using processing circuitry, a baseline of one or more operational parameters for the separator system, wherein the establishing comprises:

retrieving a data structure from memory corresponding to stored predefined expected ranges of the one or more operational parameters, wherein the stored predefined expected ranges characterize healthy blood that is without one or more of clots or occlusions, identifying a current operating state of the separator system, wherein the current operating state corresponds to observable changes between collected ranges of the one or more operational parameters and the stored predefined expected ranges of the one or more operational parameters, selecting a baseline value for the one or more operational parameters for an established baseline of the one or more operational parameters based on the identified current operating state from the expected ranges of the one or more operational parameters, and modifying operation of the separator system based on the observable changes, wherein:

modifying the operation comprises one or more of:

increasing a target operational parameter in response to detection of a blood condition asynchronous with the stored predefined expected ranges characterizing the healthy blood, or decreasing the target operational parameter in response to detection of a blood condition asynchronous to the stored predefined expected ranges characterizing the healthy blood, and the baseline value remains unaffected when the observable changes exceed a predefined frequency or a predefined range;

identifying, using the processing circuitry, at least one deviation from the established baseline of the one or more operational parameters of the separator instrument;

determining, using the processing circuitry, that the identified at least one deviation corresponds to at least one engagement condition of the separator instrument; and causing, using the processing circuitry, an action to be performed based on the determining.

2. The method of claim 1, wherein:

establishing the baseline of the one or more operational parameters comprises processing a selective data set that is representative of a heterogeneous population; and the baseline is characterized via stored predefined expected ranges that characterize healthy blood that is without one or more of clots or occlusions.

3. The method of claim 1, wherein the at least one deviation from the established baseline of the one or more operational parameters of the separator instrument comprises at least one of (a) a change in one or more of a rotational rate, a torque load, or a direction of rotation, or (b) interruptions, or pauses of operation, of the separator instrument.

4. The method of claim 1, wherein the system stores in memory communicatively coupled to the processing circuitry a maximum value corresponding to the one or more operational parameters and a minimum value corresponding to the one or more operational parameters for each respective manufactured iteration of the system, and the method further comprises:

comparing the baseline of the one or more operational parameters to the maximum value and the minimum value;

determining, based on the comparing, a value corresponding to the baseline of the one or more operational parameters exceeds the maximum value or the value is less than the minimum value; and in response to the determining, causing, using the processing circuitry, one or more of modifying the one or more operational parameters or terminating operation of the system without updating the baseline.

5. The method of claim 1, wherein the one or more operational parameters comprises a torque, and wherein establishing the baseline of the one or more operational parameters for the separator instrument comprises:

receiving a signal comprising torque information for a motorized separator; and processing the signal to calculate a baseline torque in real-time, wherein the baseline torque comprises a real-time baseline torque.

6. The method of claim 5, wherein:

the real-time baseline torque is determined based on one or more of a current torque measurement value, a previously calculated baseline torque, preclinically derived values, or values derived from previous clinical usage;

the current torque measurement value and the previously calculated baseline torque are weighted based on a total number of torque measurements received from the signal; and the real-time baseline torque is dynamically updated based on a comparison between the current torque measurement value and an amplitude threshold.

7. The method of claim 5, further comprising:

determining a dynamic threshold based on the real-time baseline torque and a previously calculated baseline torque; and determining that the at least one torque measurement is anomalous relative to the real-time baseline torque based on comparing a value of the at least one torque measurement to the dynamic threshold.

8. The method of claim 7, further comprising:

determining the at least one torque measurement that is anomalous is caused by an occlusion in a vasculature by identifying a pattern in one or more torque measurement values associated with the occlusion in the vasculature, wherein the pattern in the one or more torque measurement values associated with the occlusion in the vasculature is outside one or more of an upper limit or a lower limit of the established baseline of the one or more operational parameters.

9. A method for detecting different engagement conditions of a separator instruction of a system comprising the separator instruction, the method comprising:

establishing, using processing circuitry, a baseline of one or more operational parameters for the separator system, wherein:

the one or more operational parameters comprises a torque, establishing the baseline of the one or more operational parameters for the separator instrument comprises:

receiving a signal comprising torque information for a motorized separator; and processing the signal to calculate a baseline torque in real-time for an established baseline of the one or more operational parameters; and the established baseline of the one or more operational parameters correspond to healthy blood that is without one or more of clots or occlusions such that observable changes in collected operational data are established in response to engagement between an element of the separator system and occlusive material;

identifying, using the processing circuitry, at least one deviation from the established baseline of the one or more operational parameters of the separator instrument wherein the identifying comprises determining that one or more torque measurement values determined from the signal are anomalous relative to a baseline torque comprising the established baseline of the one or more operational parameters;

determining, using the processing circuitry, that the identified at least one deviation corresponds to at least one engagement condition of the separator instrument, wherein determining the at least one engagement condition of the separator instrument comprises distinguishing the anomalous one or more torque measurements between being caused by an occlusion in a vasculature or being caused by something other than an occlusion; and causing, using the processing circuitry, an action to be performed based on the determining.

10. A system for detecting different engagement conditions of a separator instrument of the system, the system comprising:

control circuitry communicatively coupled to the separator instrument, wherein the control circuitry is configured to transmit operational instructions to the separator instrument; and processing circuitry communicatively coupled to the control circuitry, wherein the processing circuitry is configured to:

establish a baseline of one or more operational parameters for the separator instrument, wherein the establishing comprises;

retrieving a data structure from memory corresponding to stored predefined expected ranges of the one or more operational parameters, wherein the stored predefined expected ranges characterize healthy blood that is without one or more of clots or occlusions, identifying a current operating state of the separator system, wherein the current operating state corresponds to observable changes between collected ranges of the one or more operational parameters and the stored predefined expected ranges of the one or more operational parameters, and selecting a baseline value for the one or more operational parameters based on the identified current operating state from the expected ranges of the one or more operational parameters, wherein the baseline value comprises the established baseline of the one or more operational parameters;

identify at least one deviation from the established baseline of the one or more operational parameters of the separator instrument;

determine that the identified at least one deviation corresponds to at least one engagement condition of the separator instrument; and cause an action to be performed based on the determining wherein the action comprises modifying operation of the separator system based on the observable changes, wherein modifying the operation comprises one or more of:

increasing a target operational parameter in response to detection of a blood condition asynchronous with stored predefined expected ranges characterizing the healthy blood, or decreasing the target operational parameter in response to detection of a blood condition asynchronous to stored predefined expected ranges characterizing the healthy blood;

wherein the baseline value remains unaffected when observable changes exceed a predefined frequency or a predefined range.

11. The system of claim 10, wherein:

the processing circuitry is further configured to process a selective data set that is representative of a heterogeneous population; and the processing circuitry establishes the baseline via stored predefined expected ranges that characterize healthy blood that is without one or more of clots or occlusions.

12. The system of claim 10, wherein the at least one deviation from the established baseline of the one or more operational parameters of the separator instrument comprises at least one of (a) a change in one or more of a rotational rate, a torque load, or a direction of rotation, or (b) interruptions, or pauses of operation, of the separator instrument.

13. The system of claim 10, wherein the system stores in memory communicatively coupled to the processing circuitry a maximum value corresponding to the one or more operational parameters and a minimum value corresponding to the one or more operational parameters for each respective manufactured iteration of the system, and the processing circuitry is further configured to:

compare the baseline of the one or more operational parameters to the maximum value and the minimum value;

determine, based on the comparing, a value corresponding to the established baseline of the one or more operational parameters exceeds the maximum value or the value is less than the minimum value; and in response to the determining, cause, using the processing circuitry, one or more of modifying the one or more operational parameters or terminating operation of the system without updating the established baseline.

14. The system of claim 10, wherein the one or more operational parameters comprises a torque, and wherein the processing circuitry configured to establish the baseline of the one or more operational parameters for the separator instrument is further configured to:

receive a signal comprising torque information for a motorized separator; and process the signal to calculate a baseline torque in real-time, wherein the baseline torque comprises a real-time baseline torque.

15. The system of claim 14, wherein:

the real-time baseline torque is determined by the processing circuitry based on one or more of a current torque measurement value, a previously calculated baseline torque, preclinically derived values, or values derived from previous clinical usage;

the current torque measurement value and the previously calculated baseline torque are weighted by the processing circuitry based on a total number of torque measurement values received from the signal; and the real-time baseline torque is dynamically updated using the processing circuitry based on a comparison between the current torque measurement value and an amplitude threshold.

16. The system of claim 14, wherein the processing circuitry is further configured to:

determine a dynamic threshold based on the calculated baseline torque and a previously calculated baseline torque; and determine at least one torque measurement is anomalous relative to the baseline torque based on comparing a value of the at least one torque measurement to the dynamic threshold.

17. The system of claim 16, wherein:

the processing circuitry configured to determine the at least one torque measurement is anomalous relative to the established baseline of the one or more operational parameters is further configured to determine the at least one torque measurement that is anomalous is caused by an occlusion in a vasculature by identifying a pattern in one or more torque measurement values associated with the occlusion in the vasculature; and the processing circuitry is configured to identify the pattern in the one or more torque measure values associated with the occlusion in the vasculature by determining the one or more torque measure values is outside one or more of an upper limit or a lower limit of the established baseline of the one or more operational parameters.

18. A system for detecting different engagement conditions of a separator instrument of the system, the system comprising:

control circuitry communicatively coupled to the separator instrument, wherein the control circuitry is configured to transmit operational instructions to the separator instrument; and processing circuitry communicatively coupled to the control circuitry, wherein the processing circuitry is configured to:

receive a signal comprising torque information for a motorized separator comprising the separator instrument;

process the signal to calculate a baseline torque in real-time, wherein the baseline torque comprises a real-time baseline torque;

establish a baseline of one or more operational parameters for the separator instrument based at least in part on the baseline torque, wherein:

the baseline of the one or more operational parameters is an established baseline of the one or more baseline operational parameters, the one or more operational parameters comprises a torque, and the established baseline of the one or more operational parameters correspond to healthy blood that is without one or more of clots or occlusions such that observable changes in collected operational data are established in response to engagement between an element of the separator system and occlusive material;

identify at least one deviation from the established baseline of the one or more operational parameters of the separator instrument;

determine that one or more torque measurement values determined from the signal are anomalous relative to the baseline torque;

determine that an identified at least one deviation of the one or more torque measurement values corresponds to at least one engagement condition of the separator instrument, wherein the determining comprises distinguishing the anomalous one or more torque measurements between being caused by an occlusion in a vasculature or being caused by something other than an occlusion; and cause an action to be performed based on determining that the identified at least one deviation corresponds to the at least one engagement condition of the separator instrument.

* * * * *